(12) United States Patent
Moffitt et al.

(10) Patent No.: US 7,702,385 B2
(45) Date of Patent: Apr. 20, 2010

(54) ELECTRODE CONTACT CONFIGURATIONS FOR AN IMPLANTABLE STIMULATOR

(75) Inventors: Michael A. Moffitt, Valencia, CA (US); Rafael Carbunaru, Studio City, CA (US); Todd K. Whitehurst, Santa Clarita, CA (US); Alfred E. Mann, Beverly Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 525 days.

(21) Appl. No.: 11/280,582

(22) Filed: Nov. 16, 2005

(65) Prior Publication Data

US 2007/0112403 A1    May 17, 2007

(51) Int. Cl.
*A61N 1/05* (2006.01)

(52) U.S. Cl. .............................. 607/2; 607/36; 607/46; 607/48

(58) Field of Classification Search .................... 604/20; 607/1, 2, 9, 14, 36, 45, 46, 61, 116, 48, 54, 607/5

See application file for complete search history.

(56) References Cited

U.S. PATENT DOCUMENTS

| | | | |
|---|---|---|---|
| 3,449,768 A | 6/1969 | Doyle | |
| 3,727,616 A | 4/1973 | Lenzkes | |
| 4,459,989 A | 7/1984 | Borkan | |
| 4,612,934 A | 9/1986 | Borkan | |
| 5,193,539 A | 3/1993 | Schulman et al. | |
| 5,193,540 A * | 3/1993 | Schulman et al. | 607/61 |
| 5,312,439 A | 5/1994 | Loeb | |
| 5,324,316 A | 6/1994 | Schulman et al. | |
| 5,405,367 A | 4/1995 | Schulman et al. | |
| 5,501,703 A | 3/1996 | Holsheimer et al. | |
| 5,782,891 A * | 7/1998 | Hassler et al. | 607/36 |
| 5,895,416 A | 4/1999 | Barreras, Sr. et al. | |
| 5,938,688 A | 8/1999 | Schiff | |

(Continued)

FOREIGN PATENT DOCUMENTS

WO       WO 98/37926 A1    9/1998

(Continued)

*Primary Examiner*—Carl H Layno
*Assistant Examiner*—Luther G Behringer
(74) *Attorney, Agent, or Firm*—Darby & Darby P.C.

(57) ABSTRACT

An exemplary implantable stimulator includes at least one electrode contact array and at least one additional electrode contact. Both the electrode contact array and the additional electrode contact are disposed on an external surface of the stimulator. The electrode contact array includes multiple electrode contacts that are configured to have a first polarity. The additional electrode is configured to have a second polarity. One or more of the electrode contacts disposed on the stimulator are configured to deliver monopolar stimulation and/or multipolar stimulation. Exemplary methods of stimulating a stimulation site within a patient include providing at least one electrode contact array and at least one additional electrode contact. Both the electrode contact array and the additional electrode contact are disposed on an external surface of the stimulator. The electrode contact array includes multiple electrode contacts that are configured to have a first polarity. The additional electrode is configured to have a second polarity. The method further includes applying an electrical stimulation current to the stimulation site via one or more of the electrode contacts that are disposed on the stimulator.

38 Claims, 16 Drawing Sheets

U.S. PATENT DOCUMENTS

| | | | |
|---|---|---|---|
| 5,941,906 | A | 8/1999 | Barreras, Sr. et al. |
| 6,016,449 | A | 1/2000 | Fischell et al. |
| 6,051,017 | A | 4/2000 | Loeb et al. |
| 6,052,624 | A | 4/2000 | Mann |
| 6,164,284 | A | 12/2000 | Schulman et al. |
| 6,185,452 | B1 * | 2/2001 | Schulman et al. ............. 604/20 |
| 6,208,894 | B1 | 3/2001 | Schulman et al. |
| 6,214,032 | B1 * | 4/2001 | Loeb et al. ...................... 607/1 |
| 6,219,580 | B1 | 4/2001 | Faltys et al. |
| 6,272,382 | B1 | 8/2001 | Faltys et al. |
| 6,280,873 | B1 | 8/2001 | Tsukamoto |
| 6,308,101 | B1 | 10/2001 | Faltys et al. |
| 6,381,496 | B1 | 4/2002 | Meadows et al. |
| 6,393,325 | B1 | 5/2002 | Mann et al. |
| 6,458,171 | B1 | 10/2002 | Tsukamoto |
| 6,487,446 | B1 | 11/2002 | Hill et al. |
| 6,516,227 | B1 | 2/2003 | Meadows et al. |
| 6,539,263 | B1 | 3/2003 | Schiff et al. |
| 6,553,263 | B1 | 4/2003 | Meadows et al. |
| 6,622,048 | B1 | 9/2003 | Mann et al. |
| 6,662,053 | B2 | 12/2003 | Borkan |
| 6,760,626 | B1 | 7/2004 | Boveja |
| 6,920,359 | B2 | 7/2005 | Meadows et al. |
| 6,925,334 | B1 * | 8/2005 | Salys ........................ 607/116 |
| 2001/0046625 | A1 | 11/2001 | Ruth, II et al. |
| 2001/0053476 | A1 | 12/2001 | Ruth et al. |
| 2002/0062141 | A1 * | 5/2002 | Moore ......................... 607/60 |
| 2002/0107547 | A1 * | 8/2002 | Erlinger et al. ................ 607/5 |
| 2003/0120316 | A1 * | 6/2003 | Spinelli et al. ................ 607/14 |
| 2004/0034394 | A1 * | 2/2004 | Woods et al. ................ 607/46 |
| 2004/0073270 | A1 * | 4/2004 | Firlik et al. ................... 607/48 |
| 2004/0162590 | A1 * | 8/2004 | Whitehurst et al. ........... 607/17 |
| 2005/0113894 | A1 * | 5/2005 | Zilberman et al. .......... 607/116 |
| 2005/0197675 | A1 * | 9/2005 | David et al. ................... 607/9 |
| 2006/0206162 | A1 * | 9/2006 | Wahlstrand et al. .......... 607/46 |

FOREIGN PATENT DOCUMENTS

| | | | |
|---|---|---|---|
| WO | WO 98/43700 | A1 | 10/1998 |
| WO | WO 98/43701 | A1 | 10/1998 |
| WO | WO 01/82398 | A1 | 1/2001 |
| WO | WO 03/005465 | A1 | 1/2003 |
| WO | WO 2007/059343 | * | 5/2007 |

* cited by examiner

ELECTRODE CONTACT CONFIGURATIONS FOR AN IMPLANTABLE STIMULATOR

BACKGROUND

A wide variety of medical conditions and disorders have been successfully treated using an implantable stimulator. Implantable stimulators typically stimulate internal tissue, such as a nerve, by emitting an electrical stimulation current according to programmed stimulation parameters.

One type of implantable stimulator is known as a microstimulator. Microstimulators are typically characterized by a small, cylindrical housing containing electronic circuitry that produces the desired electric stimulation current between spaced electrodes. These stimulators are implanted proximate to the target tissue so that the stimulation current produced by the electrodes stimulates the target tissue to reduce symptoms or otherwise provide therapy for a wide variety of conditions and disorders. Exemplary microstimulators are described in U.S. Pat. Nos. 5,312,439; 5,193,539; 5,193,540; and 5,405,367; 6,185,452; and 6,214,032. All of these listed patents are incorporated by reference in their respective entireties.

Another type of implantable stimulator is known as an implantable pulse generator (IPG). A typical IPG includes a multi-channel pulse generator housed in a rounded titanium case. The IPG is generally coupled to a lead with a number of electrodes disposed thereon. Stimulation current is generated by the IPG and delivered to target tissue via the electrodes on the lead. Exemplary IPGs are described in U.S. Pat. Nos. 6,381,496; 6,553,263; and 6,760,626. All of these listed patents are incorporated by reference in their respective entireties.

As will be readily appreciated, a key part of patient treatment using an implanted stimulator is the proper placement of the stimulator such that the stimulation electrodes are proximate to the stimulation site to be stimulated. If the stimulation electrodes are optimally placed near the stimulation site, stimulation can be affected over a wide range of parameters and power consumption can be minimized. However, optimal placement of a stimulator within a patient is often difficult to accomplish.

SUMMARY

An exemplary implantable stimulator includes at least one electrode contact array and at least one additional electrode contact. Both the electrode contact array and the additional electrode contact are disposed on an external surface of the stimulator. The electrode contact array includes multiple electrode contacts that are configured to have a first polarity. The additional electrode is configured to have a second polarity. One or more of the electrode contacts disposed on the stimulator are configured to deliver monopolar stimulation and/or multipolar stimulation.

Exemplary methods of stimulating a stimulation site within a patient include providing at least one electrode contact array and at least one additional electrode contact. Both the electrode contact array and the additional electrode contact are disposed on an external surface of the stimulator. The electrode contact array includes multiple electrode contacts that are configured to have a first polarity. The additional electrode is configured to have a second polarity. The method further includes applying an electrical stimulation current to the stimulation site via one or more of the electrode contacts that are disposed on the stimulator.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

An implantable stimulator configured to stimulate a stimulation site with monopolar and/or multipolar stimulation is described herein. The stimulator includes at least one electrode contact array and at least one additional electrode contact. Both the electrode contact array and the additional electrode contact are disposed on an external surface of the stimulator. The electrode contact array includes multiple electrode contacts that are configured to have a first polarity. The additional electrode is configured to have a second polarity. One or more of the electrode contacts disposed on the stimulator are configured to deliver monopolar stimulation and/or multipolar stimulation.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

As used herein and in the appended claims, the term "stimulator" will be used broadly to refer to any type of device that is implanted to deliver a stimulus to a stimulation site within a patient. As used herein and in the appended claims, unless otherwise specifically denoted, the term "stimulation site" will be used to refer to any nerve, muscle, organ, or other tissue within a patient that is stimulated by an implantable stimulator. For example, in the case of urinary incontinence, the stimulation site may be, but is not limited to, any nerve or muscle in the pelvic floor. Stimulation sites in the pelvic floor region that may be targeted for stimulation include, but are not limited to, the pudendal nerve, pelvic nerve, and the clitoral branches of the pudendal nerve.

The stimulus applied to the stimulation site may include electrical stimulation, also known as neuromodulation. Electrical stimulation will be described in more detail below. Consequently, the terms "stimulus" and "stimulation" will be used interchangeably herein and in the appended claims, unless otherwise specifically denoted, to refer to electrical stimulation.

Figure 1:
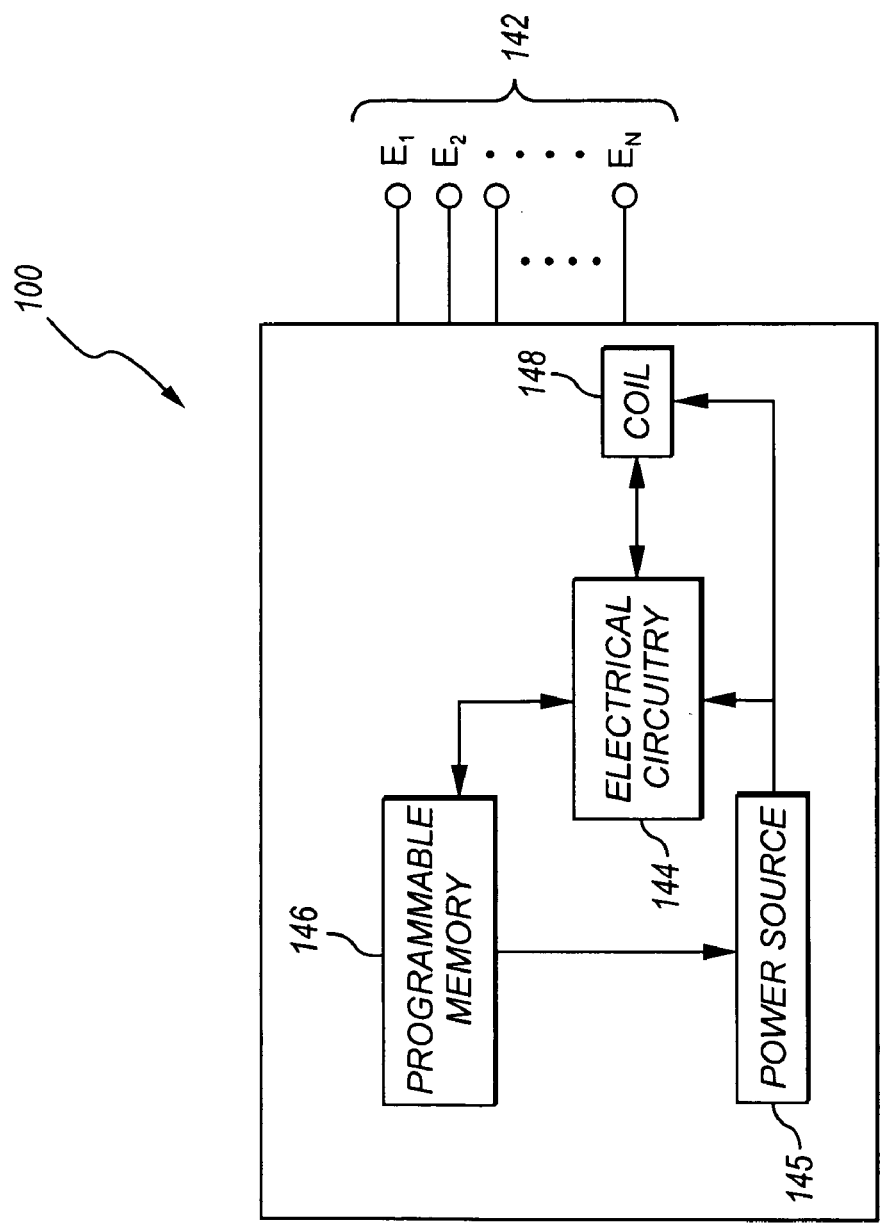
FIG. 1 is a block diagram illustrating a number of components of an exemplary implantable stimulator according to principles described herein.

Turning to the drawings, FIG. 1 is a block diagram illustrating a number of components of an exemplary implantable stimulator (100). The components of the stimulator (100) of FIG. 1 may be similar to the components included within a BION® microstimulator (Advanced Bionics® Corporation, Valencia, Calif.), for example. Various details associated with the manufacture, operation, and use of BION implantable microstimulators are disclosed in U.S. Pat. Nos. 5,193,539; 5,193,540; 5,312,439; 6,185,452; 6,164,284; 6,208,894; and 6,051,017 and in U.S. application Ser. No. 10/609,457. All of these listed patents and the listed patent application are incorporated herein by reference in their respective entireties.

The stimulator (100) if FIG. 1 may alternatively include an implantable pulse generator (IPG), spinal cord stimulator (SCS), or deep brain stimulator. Exemplary IPGs suitable for use as described herein include, but are not limited to, those disclosed in U.S. Pat. Nos. 6,381,496; 6,553,263; and 6,760,626. Exemplary spinal cord stimulators suitable for use as described herein include, but are not limited to, those disclosed in U.S. Pat. Nos. 5,501,703; 6,487,446; and 6,516,227. Exemplary deep brain stimulators suitable for use as described herein include, but are not limited to, those disclosed in U.S. Pat. Nos. 5,938,688; 6,016,449; and 6,539,263. All of these listed patents are incorporated herein by reference in their respective entireties.

As shown in FIG. 1, the stimulator (100) may include a power source (145), a programmable memory (146), electrical circuitry (144), a pump (147), and a coil (148). It will be recognized that the stimulator (100) may include additional and/or alternative components as best serves a particular application.

The power source (145) is configured to output a voltage used to supply the various components within the stimulator (100) with power and/or to generate the power used for electrical stimulation. The power source (145) may be a primary battery, a rechargeable battery, super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like. Alternatively, the stimulator (100) may include one or more components configured to receive power from another medical device that is implanted within the patient.

When the power source (145) is a battery, it may be a lithium-ion battery or other suitable type of battery. When the power source (145) is a rechargeable battery, it may be recharged from an external system through a power link such as a radio frequency (RF) power link. One type of rechargeable battery that may be used is described in International Publication WO 01/82398 A1, published Nov. 1, 2001, and/or WO 03/005465 A1, published Jan. 16, 2003, both of which are incorporated herein by reference in their entireties. Other battery construction techniques that may be used to make a power source (145) include those shown, e.g., in U.S. Pat. Nos. 6,280,873; 6,458,171, and U.S. Application Publication Nos. 2001/0046625 A1 and 2001/0053476 A1, all of which are incorporated herein by reference in their respective entireties. Recharging can be performed using an external charger.

The stimulator (100) may also include a coil (148) configured to receive and/or emit a magnetic field (also referred to as a radio frequency (RF) field) that is used to communicate with or receive power from one or more external devices that support the implanted stimulator (100), examples of which will be described below. Such communication and/or power transfer may include, but is not limited to, transcutaneously receiving data from the external device, transmitting data to the external device, and/or receiving power used to recharge the power source (145).

The stimulator (100) may also include electrical circuitry (144) configured to produce electrical stimulation pulses that are delivered to the stimulation site via a number of electrodes (142). In some embodiments, as will be described in more detail below, the stimulator (100) may be configured to produce monopolar stimulation. The stimulator (100) may alternatively or additionally be configured to produce multipolar stimulation including, but not limited to, bipolar or tripolar stimulation.

The electrical circuitry (144) may include one or more processors configured to decode stimulation parameters and generate the corresponding stimulation pulses. In some embodiments, the stimulator (100) has at least four channels and drives up to sixteen electrodes or more. The electrical circuitry (144) may include additional circuitry such as capacitors, integrated circuits, resistors, coils, and the like configured to perform a variety of functions as best serves a particular application.

The stimulator (100) may also include a programmable memory unit (146) for storing one or more sets of data and/or stimulation parameters. The stimulation parameters may include, but are not limited to, electrical stimulation parameters and other types of stimulation parameters. The programmable memory (146) allows a patient, clinician, or other user of the stimulator (100) to adjust the stimulation parameters such that the stimulation applied by the stimulator (100) is safe and efficacious for a particular medical condition and/or for a particular patient. The programmable memory (146) may be any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, electrode configuration (i.e., anode-cathode assignment), burst pattern (e.g., burst on time and burst off time), duty cycle or burst repeat interval, ramp on time, and ramp off time of the stimulation current that is applied to the stimulation site.

Specific stimulation parameters may have different effects on neural or other tissue. Thus, in some embodiments, the stimulation parameters may be adjusted by the patient, a clinician, or other user of the stimulator (100) as best serves a particular stimulation site. The stimulation parameters may also be automatically adjusted by the stimulator (100), as will be described below. For example, the amplitude of the stimulation current applied to a stimulation site may be adjusted to have a relatively low value to target a nerve having relatively large diameter fibers. The stimulator (100) may also, or alternatively, increase excitement of a stimulation site by applying a stimulation current having a relatively low frequency to the stimulation site (e.g., less than 100 Hz). The stimulator (100) may also or alternatively decrease excitement of a stimulation site by applying a relatively high frequency to the stimulation site (e.g., greater than 100 Hz). The stimulator (100) may also, or alternatively, be programmed to apply the stimulation current to a stimulation site intermittently or continuously.

As shown in FIG. 1, the stimulator (100) may be coupled to a number of electrodes or electrode contacts $E_1$-$E_n$ (142) configured to apply the electrical stimulation current to the stimulation site. As shown in FIG. 1, there may be any number of electrodes (142) as best serves a particular application. In some examples, one or more of the electrodes (142) may be designated as stimulating electrodes and one of the electrodes (142) may be designated as an indifferent electrode used to complete one or more stimulation circuits. In some embodiments, as will be described in more detail below, the electrodes (142) are leadless and are disposed on or coupled to the body of the stimulator (100). The electrodes (142) may alternatively be a part of a lead that is coupled to the body of the stimulator (100). The electrodes (142) will be described in more detail below.

Figure 2:
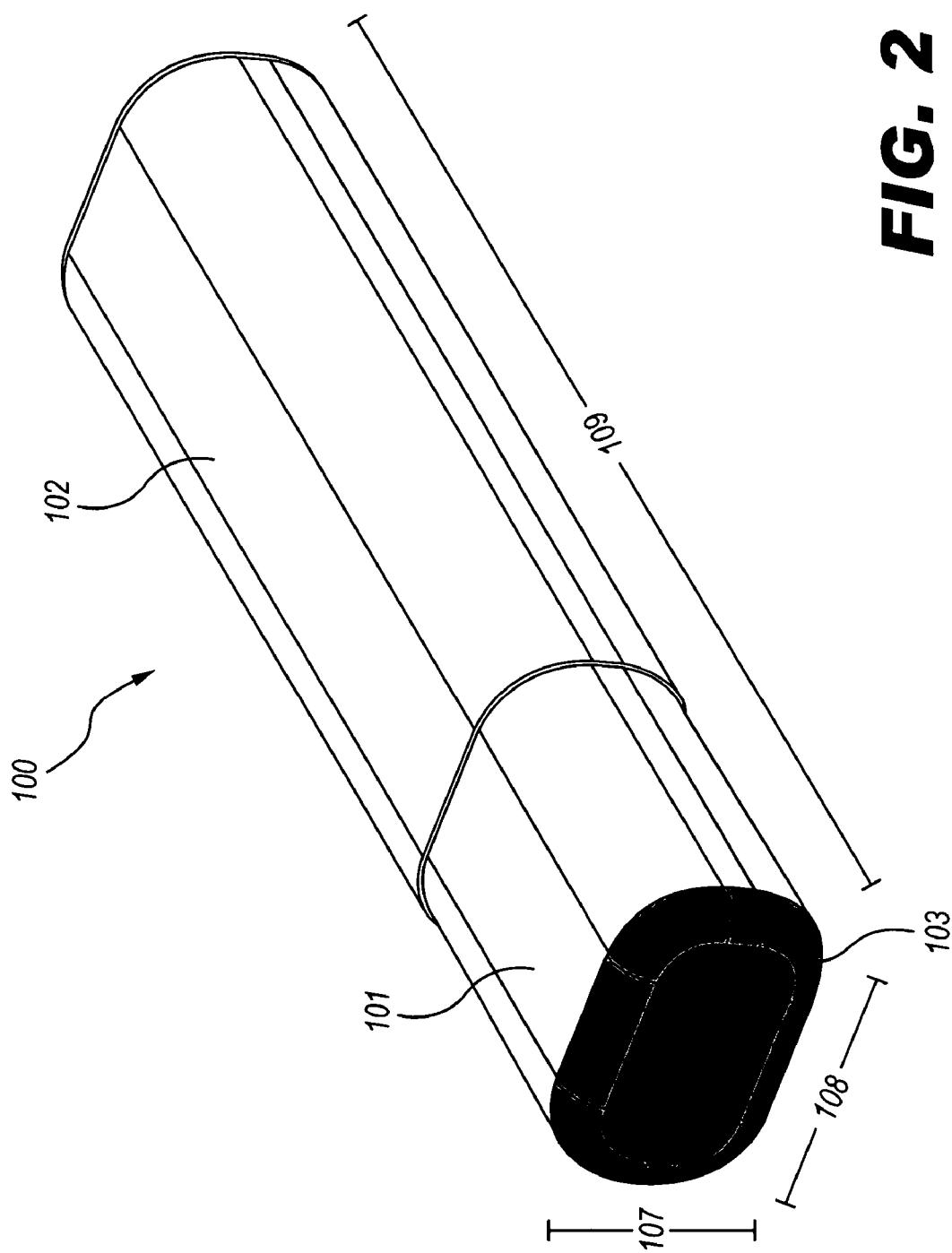
FIG. 2 illustrates an exemplary structure of the implantable stimulator according to principles described herein.

FIG. 2 illustrates an exemplary structure of the implantable stimulator (100). In some embodiments, as shown in FIG. 2, the stimulator (100) has a rectangular cross-section with corner rounding. The rectangular cross-section shape of the stimulator (100) allows the stimulator (100) to be implanted within a patient in a pre-determined orientation. In addition, the slightly significant aspect ratio (cross-section) of the stimulator (100) minimizes the profile, or height (107), of the stimulator (100), which reduces implantation discomfort and skin erosion in many patients. The minimized height (107) also improves the aesthetic appeal of the stimulator (100) when implanted. It will be recognized, however, that the rectangular shape of the stimulator (100) shown in FIG. 2 is merely exemplary of the many different dimensional configurations of the stimulator (100). For example, the stimulator (100) may have a cylindrical shape, a long oval shape, or any other shape currently used in already-existing stimulators.

As shown in FIG. 2, the stimulator (100) has a height (107), width (108), and length (109). An exemplary height (107) is substantially equal to 4.25 millimeters (mm), an exemplary width (108) is substantially equal to 7.25 mm, and an exemplary length (109) is substantially equal to 28 mm. It will be recognized that these dimensions are merely illustrative and that the dimensions of the stimulator (100) may be greater or less than the exemplary dimensions given as best serves a particular application.

In some embodiments, the length (109) of the stimulator (100) is longer than conventional stimulators so that the power source (145; FIG. 1) may be relatively larger than power supplies in conventional stimulators. A relatively large power source (145; FIG. 1) may serve to reduce the recharging frequency of the stimulator (100).

As shown in FIG. 2, the stimulator (100) may include multiple assemblies. For example, the stimulator (100) may include a first assembly (101) coupled to a second assembly (102). Each assembly may be configured to house different components of the stimulator (100).

In some examples, the first assembly (101) houses the electrical circuitry (144; FIG. 1), the programmable memory (146; FIG. 1), the coil (148; FIG. 1), the pump (147; FIG. 1), and/or any other components of the stimulator (100) as best serves a particular application. The first assembly (101) may be made out of any suitable material that allows the coil (148;

FIG. 1) to emit and receive a magnetic field used to communicate with an external device or with another implanted device. For example, the first assembly (101) may be made out of a ceramic material, glass, plastic, a polymer, a metal (e.g., Titanium) configured to allow the passage of a magnetic field, or any other suitable material. Because the first assembly (101) is sometimes made out of a ceramic material, it is sometimes referred to as a ceramic tube assembly.

The second assembly (102) shown in FIG. 2 houses the power source (145; FIG. 1). The second assembly (102) has a cross section substantially equal to the cross section of the first assembly (101). The second assembly (102) may be made out of any insulative material such as ceramic or glass. The second assembly (102) may additionally or alternatively include a non-conductive coating, such as, but not limited to, PARYLENE™ or TEFLON™. In some alternative embodiments, the second assembly (102) is made out of a conductive metal (e.g., titanium). A metal housing allows the second assembly (102) to be relatively thin, thereby maximizing the space within the second assembly (102) for the power source (145; FIG. 1).

In some examples, the stimulator (100) may also include a cap assembly (103) at either end of the stimulator body. The cap assembly may be made out of any suitable material such as, but not limited to, a ceramic material, glass, plastic, a polymer, or a metal (e.g., Titanium).

For illustrative purposes only, it will be assumed in the examples given herein that the stimulator (100) includes a first assembly (101), a second assembly (102), and a cap assembly (103), as described in connection with FIG. 2. However, it will be recognized that the stimulator (100) may include any number of assemblies made out of any combination of materials. For example, the stimulator (100) may only include a single assembly that houses all the components of the stimulator (100). Alternatively, the stimulator (100) may include more than two assemblies. In general, the external surface of the stimulator (100) may be made out of glass, ceramic, plastic, polymers, metal, metal-alloys, or any other suitable material.

As mentioned, the stimulator (100) may be configured to provide monopolar and/or multipolar electrical stimulation to a stimulation site via a number of electrodes (142; FIG. 1). Each electrode (142; FIG. 1) may be selectively configured to act as an anode or as a cathode. Monopolar stimulation is achieved by placing an electrode acting as a cathode (or anode) adjacent to or near a stimulation site, and placing an electrode of opposite polarity relatively "far away" from the stimulation site. Multipolar stimulation is achieved by placing a number of anodes and cathodes adjacent to or near a stimulation site. For example, bipolar stimulation is achieved by placing an anode-cathode pair adjacent to or near a stimulation site. Tripolar stimulation is achieved by placing a cathode surrounded by two anodes or an anode surrounded by two cathodes adjacent to or near a stimulation site.

Figure 3:
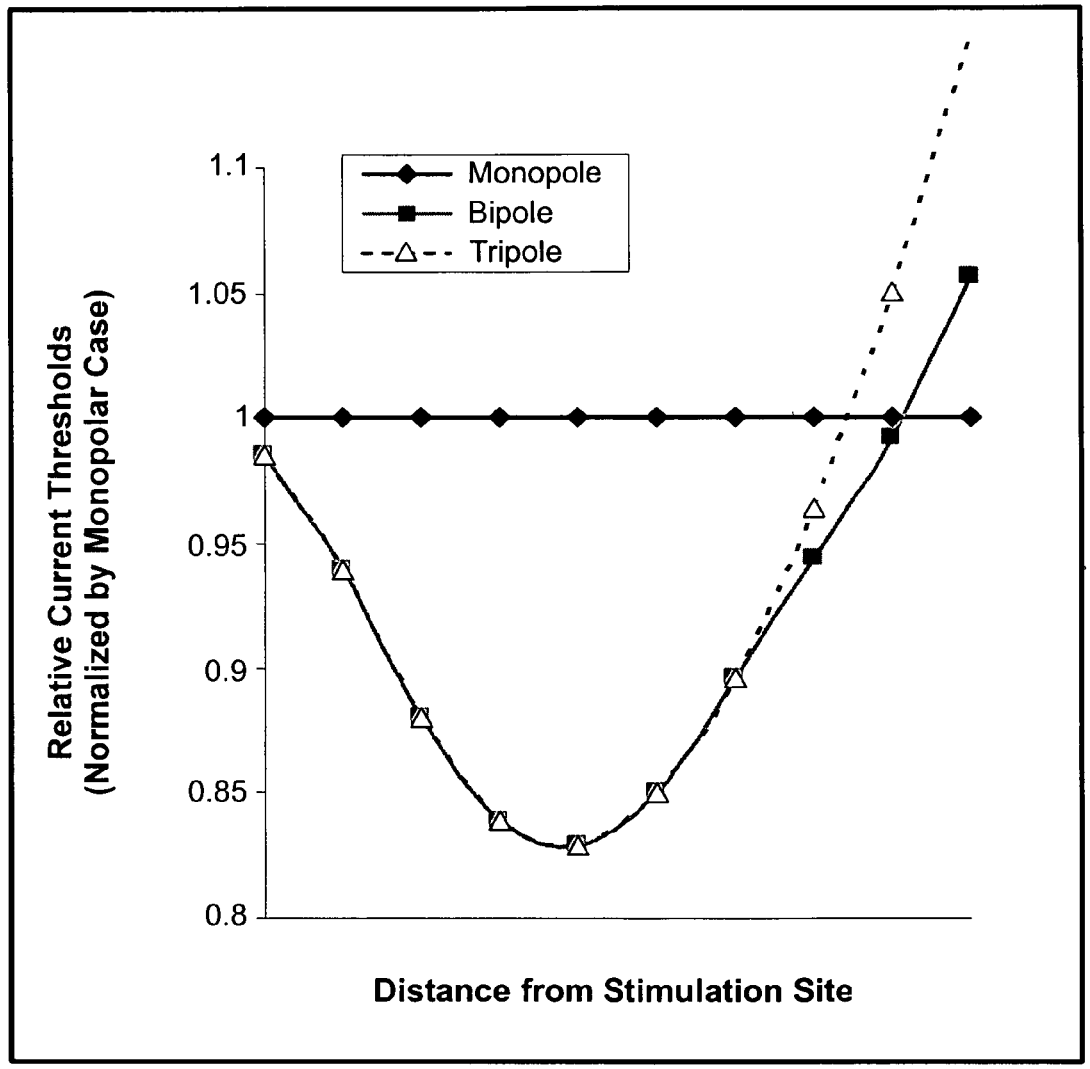
FIG. 3 is a graph illustrating the relative current threshold values of monopolar, bipolar, and tripolar electrode configurations as a function of distance from the stimulation site.

Monopolar and multipolar electrode configurations have different stimulation properties. For example, as illustrated in FIG. 3, relative current threshold values vary as a function of distance from the stimulation site for each of these electrode configurations. As used herein and in the appended claims, the term "current threshold value" will be used to refer to the minimum amount of current required to stimulate a stimulation site. FIG. 3 is a graph illustrating the relative current threshold values of monopolar, bipolar, and tripolar electrode configurations as a function of distance from the stimulation site. The graph is based on a theoretical mathematical model of neural stimulation. The current threshold values are normalized by the current threshold of the monopolar configuration.

As shown in FIG. 3, when the stimulation site is relatively near the stimulator (100; FIG. 1), lower stimulation thresholds may be achieved with a properly spaced bipole or tripole electrode configuration than with a monopole electrode configuration. However, as the distance between the stimulation site and the stimulator (100; FIG. 1) increases, the thresholds for the bipolar and tripolar electrode configurations begin to exceed that of the monopolar electrode configuration. Thus, monopolar stimulation is often used when the stimulation site is relatively "far" from the stimulator (100; FIG. 1) and multipolar stimulation is often used when the stimulation site is relatively "close" to the stimulator (100; FIG. 1).

Additionally, monopolar and multipolar electrode configurations often have different stimulation localization properties. For example, a monopolar electrode configuration emits a multidirectional electrical field that may be used to stimulate a relatively general stimulation site. A multipolar electrode configuration, on the other hand, emits a more localized electrical field that is often used to stimulate a relatively specific stimulation site, and may be used to stimulate stimulation sites that have a particular orientation.

A number of electrode arrangements that may be used to apply monopolar and/or multipolar stimulation to one or more stimulation sites will now be described in connection with FIGS. 4A-12B. Each of the electrodes described herein are coupled directly to the external surface of the stimulator (100; FIG. 2). Hence, the electrodes will also be referred to herein and in the appended claims, unless otherwise specifically denoted, as "electrode contacts" or simply "contacts."

The electrode contacts described in the following examples and in the appended claims may be made of a conducting ceramic, conducting polymer, copper, and/or a noble or refractory metal, such as gold, silver, platinum, iridium, tantalum, titanium, titanium nitride, niobium, and/or an alloy thereof. The use of one or more of these materials in constructing the electrode contacts may serve to minimize corrosion, electrolysis, and/or damage to surrounding tissues. The surfaces of the electrode contacts may have any of a number of properties. For example, the surfaces may be smooth or rough. A rough surface increases the actual surface area of an electrode contact and may, with some materials (e.g., platinum or iridium), increase the pseudo-capacitance of the electrode contact. An increased pseudo-capacitance may serve to minimize the risk of adverse electrical affects to a patient being treated.

Moreover, the electrode contacts may have any suitable size or shape. Differently shaped electrode contacts provide different current densities. For example, an oval electrode contact may provide a more uniform current density than an electrode contact that is rectangular. Hence, the shape of the electrode contacts may vary as best serves a particular application.

Figure 4A:
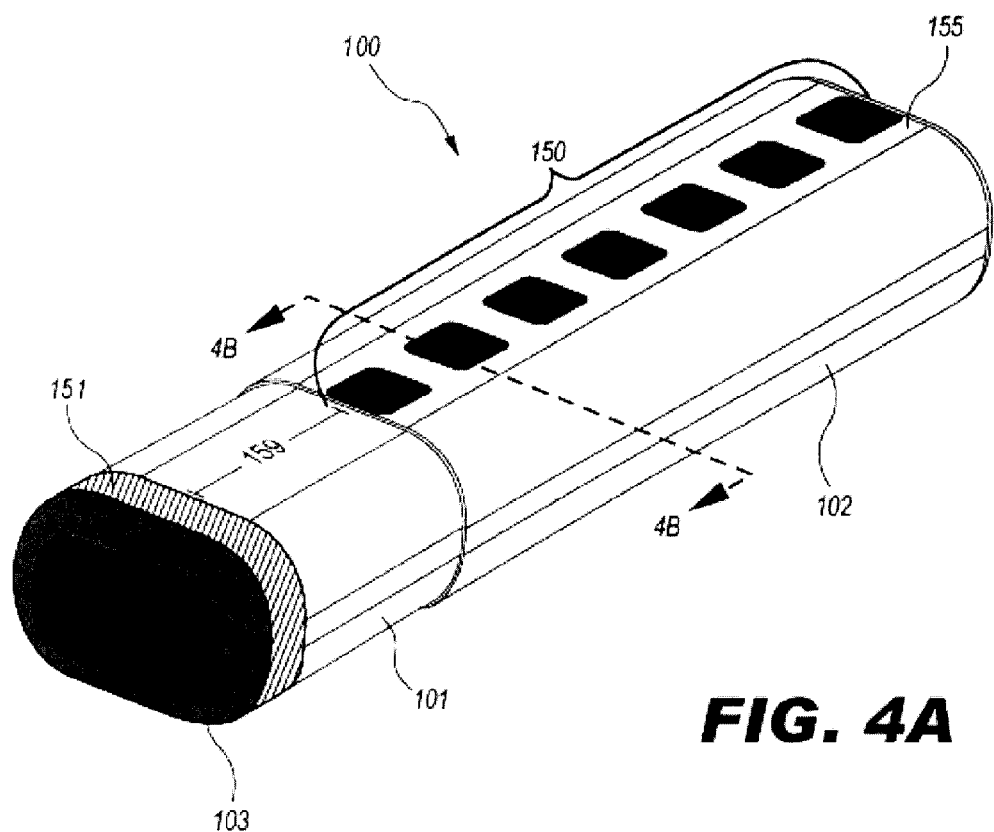
FIG. 4A is an assembled perspective view of the stimulator with an exemplary electrode contact arrangement that may be used to provide monopolar and/or multipolar stimulation to a stimulation site according to principles described herein.
Figure 4B:
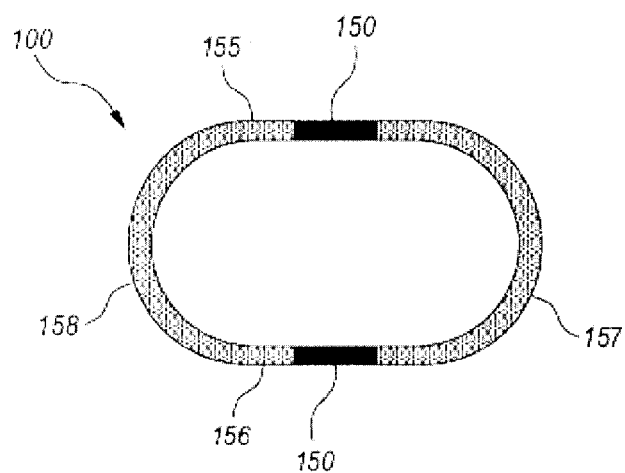
FIG. 4B is a cross-sectional view of the stimulator taken along the perspective line indicated in FIG. 4A according to principles described herein.

FIG. 4A is an assembled perspective view of the stimulator (100) with an exemplary electrode contact arrangement that may be used to provide monopolar and/or multipolar stimulation to a stimulation site. As shown in FIG. 4A, one or more arrays of cathodic electrode contacts (150) (also referred to herein and in the appended claims, unless otherwise specifically denoted, as "cathodes") are included on the external surface of the stimulator (100). For example, an array of cathodes (150) may be located along a top flat surface (155) of the stimulator (100). However, as will be shown in FIG. 4B, the array of cathodes (150) may additionally or alternatively be located along a bottom flat surface (156; FIG. 4B) of the stimulator (100).

The cathode array (150) of FIG. 4A includes eight electrode contacts aligned in a single row for illustrated purposes only. It will be recognized that each array of cathodes (150) may include any number of individual electrode contacts of any suitable size as best serves a particular application. Moreover, it will be recognized that the spacing in between each electrode contact within the array (150) may vary as best serves a particular application.

As shown in FIG. 4A, the array of cathodes (150) is arranged such that the row of electrode contacts within the array (150) is in parallel with the length of the stimulator (100). The cathode array (150) may extend along any portion of the stimulator (100). For example, the array of cathodes (150) in FIG. 4A extends along the length of the second assembly (102). However, it will be recognized that the array may also extend along a portion of the first assembly (101) as best serves a particular application.

In addition to the array of cathodes (150), an anodic electrode contact (151) (also referred to herein and in the appended claims, unless otherwise specifically denoted, as an "anode") is included on the external surface of the stimulator (100). In some examples, as shown in FIG. 4A, the anode (151) surrounds a portion, or all, of the perimeter of the stimulator (100). An electrode contact that surrounds a portion, or all, of the perimeter of the stimulator (100), such as the anode (151) shown in FIG. 4A, will be referred to herein and in the appended claims, unless otherwise denoted, as a "ring electrode contact." The anode (151) may additionally or alternatively include a portion of the cap assembly (103).

As shown in FIG. 4A, the anode (151) may be separated by a distance (159) from the array of cathodes (150) to achieve monopolar stimulation. The distance (159) may be adjusted as best serves a particular application to achieve monopolar stimulation.

FIG. 4B is a cross-sectional view of the stimulator (100) taken along the perspective line indicated in FIG. 4A that illustrates an exemplary location of the array of cathodes (150) and the anode (151). Stimulator (100) includes a top flat surface (155), a bottom flat surface (156), a first rounded side surface (157), and a second rounded side surface (158). Two arrays of cathodes (150) and one anode (151) are shown for illustrative purposes. It will be recognized that there may be any number of suitable arrays of cathodes (150) and any number of anodes (151) as best serves a particular application.

As shown in FIG. 4B, an array of cathodes (150) may be located along the top flat surface (155) and/or along the bottom flat surface (156) of the stimulator (100). Additionally or alternatively, an array of cathodes (150) may be located along the first and/or second rounded side surfaces (157, 158). FIG. 4A also shows that the anode (151) surrounds at least a portion of the perimeter of the stimulator (100).

The arrays of cathodes (150) are shown to be centered along the width of the stimulator (100) for illustrative purposes only. However, it will be recognized that one or more of the arrays of cathodes (150) may be offset by any suitable distance from the center of the width of the stimulator (100) as best serves a particular application.

Each of the electrode contacts in the cathode arrays (150) may be individually controlled. For example, one or more of the electrode contacts in the cathode arrays (150) may be designated as stimulating electrodes through which stimulation current is applied to one or more stimulation sites.

Moreover, one or more of the electrode contacts within the arrays of cathodes (150) may be configured to act as an anode. Hence, in some examples, one or more of the arrays of cathodes (150) may simultaneously include one or more electrodes acting as anodes and one or more electrodes acting as cathodes. Likewise, the anodic electrode contact (151) may be configured to act as a cathode. In this manner, any one or more of the electrode contacts located on the stimulator (100) may be used to stimulate one or more stimulation sites.

Figure 5A:
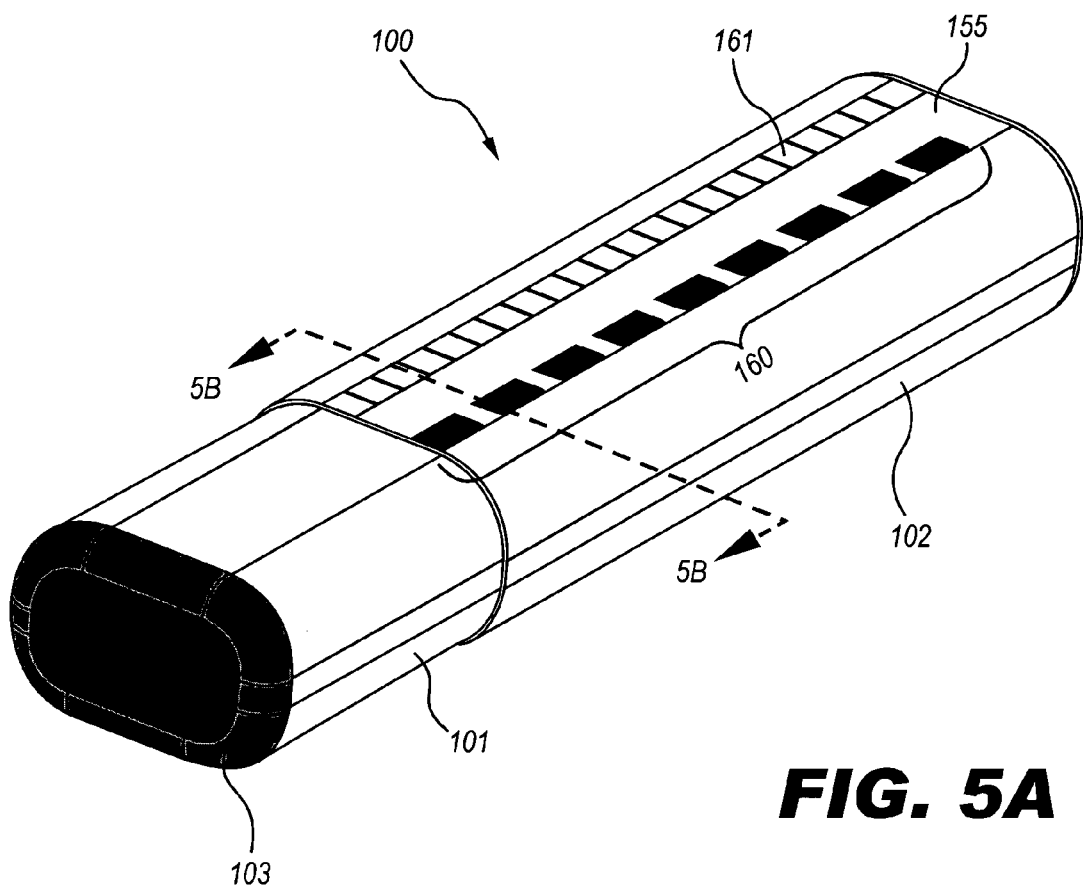
FIG. 5A is an assembled perspective view of the stimulator which illustrates another exemplary electrode contact arrangement that may be used to provide multipolar stimulation to a stimulation site which illustrates another exemplary electrode contact arrangement.
Figure 5B:
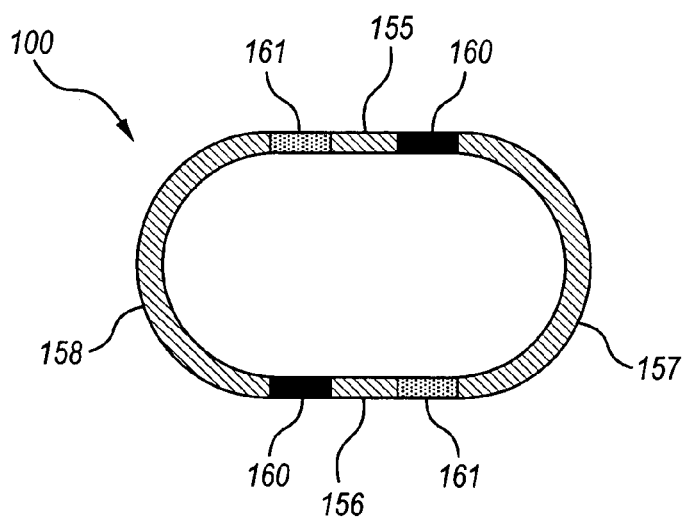
FIG. 5B is a cross-sectional view of the stimulator taken along the perspective line indicated in FIG. 5A according to principles described herein.

FIG. 5A is an assembled perspective view of the stimulator (100) which illustrates another exemplary electrode contact arrangement that may be used to provide multipolar stimulation to a stimulation site. As shown in FIG. 5A, an array of cathodes (160), similar to the array of cathodes (150) described in connection with FIG. 4A, and an anodic electrode contact (anode) (161) are located along the top flat surface (155) of the stimulator (100). As will be shown in FIG. 5B, the cathode array (160) and anode (161) may additionally or alternatively be located along the bottom flat surface (156; FIG. 5B) of the stimulator (100).

FIG. 5B is a cross-sectional view of the stimulator (100) of FIG. 5A taken along the perspective line indicated in FIG. 5A that illustrates an exemplary location of the array of cathodes (160) and the anode (161). As shown in FIG. 5B, the cathode array (160) and the anode (161) may be located along the top flat surface (155) and/or along the bottom flat surface (156) of the stimulator. Additionally or alternatively, an array of cathodes (160) and/or an anode (161) may be located along the first and/or second rounded side surfaces (157, 158).

As shown in FIG. 5B, each cathode array (160) is separated by a distance from its nearest anode (161). The distance between each cathode array (160) and its nearest anode (161) may be adjusted to minimize a threshold current value and/or achieve different bipolar stimulation characteristics. For example, in some applications, a minimum threshold current corresponding to a stimulation site 5 millimeters (mm) away from the stimulator (100) maybe achieved when the distance between each cathode array (160) and its nearest anode (161) is substantially equal to 6 mm.

Each anode (161) in FIG. 5B may be selectively switched on or off so that bipolar stimulation may be delivered to a stimulation site located near either the top or bottom sides (155, 156) of the stimulator (100). For example, the anode (161) located along the bottom surface (156) of the stimulator (100) may be switched off when it is desired to deliver bipolar stimulation only to a stimulation site near the top surface (155) of the stimulator (100). Likewise, the anode (161) located along the top surface (155) may be switched off when it is desired to deliver bipolar stimulation only to a stimulation site near the bottom surface (156) of the stimulator (100).

Each array of cathodes (160) in FIG. 5B may also be selectively switched on or off so that monopolar and/or bipolar stimulation may be delivered to a stimulation site located near either the top or bottom sides (155, 156) of the stimulator (100). For example, the cathode array (160) located along the top surface (155) of the stimulator (100) may be active and the cathode array (160) located along the bottom surface (156) of the stimulator (100) may be turned off. In this case, bipolar stimulation may be achieved by activating the anode (161) located along the top surface (155) of the stimulator (100) and monopolar stimulation may be achieved by activating the anode (161) located along the bottom surface (156) of the stimulator (100).

Each of the electrode contacts in the cathode arrays (160) may also be individually controlled. For example, one or more of the electrode contacts in the cathode arrays (160) may be designated as stimulating electrodes through which stimulation current is applied to one or more stimulation sites.

Moreover, one or more of the electrode contacts within the arrays of cathodes (160) may be configured to act as an anode. Hence, in some examples, one or more of the arrays of cathodes (160) may simultaneously include one or more electrodes acting as anodes and one or more electrodes acting as cathodes. Likewise, one or more of the anodic electrode contacts (161) may be configured to act as a cathode. In this manner, any one or more of the electrode contacts located on the stimulator (100) may be used to stimulate one or more stimulation sites.

Figure 5C:
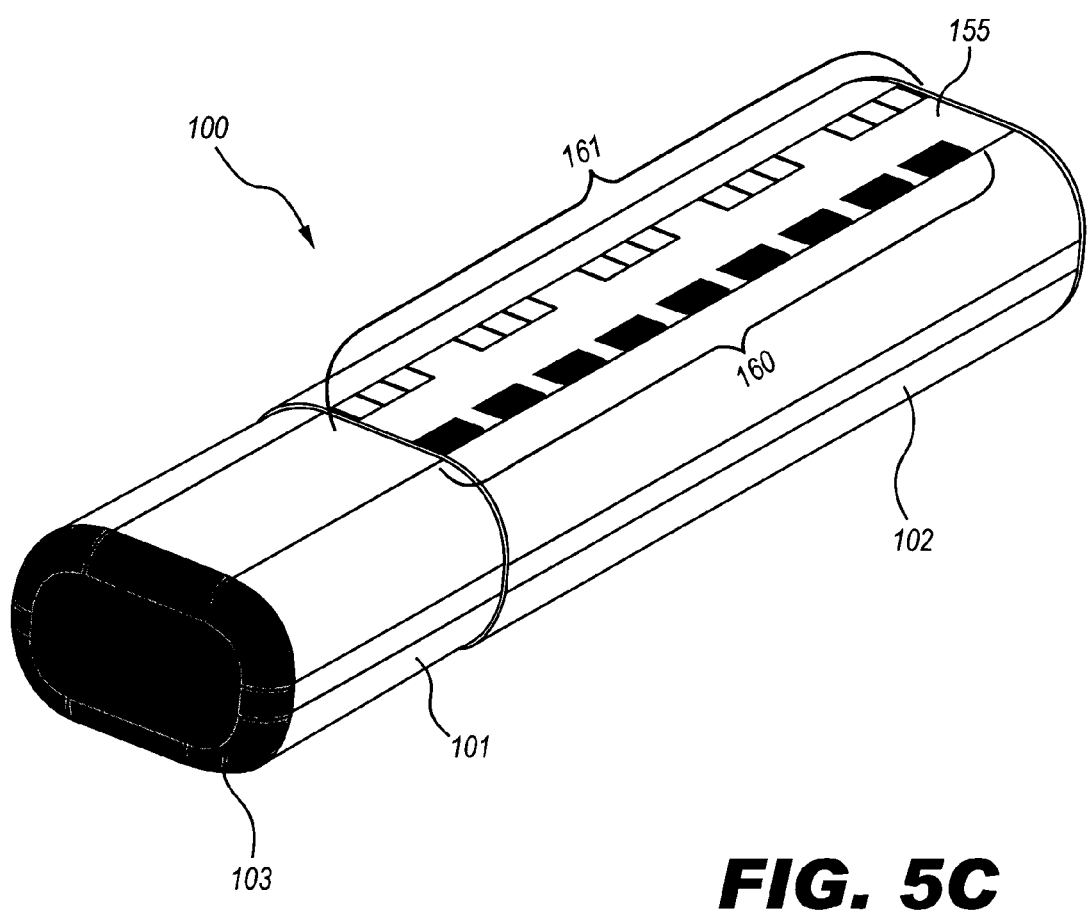
FIG. 5C is an assembled perspective view of the stimulator which illustrates that the anode may alternatively include an array of individual electrode contacts according to principles described herein.
Figure 6:
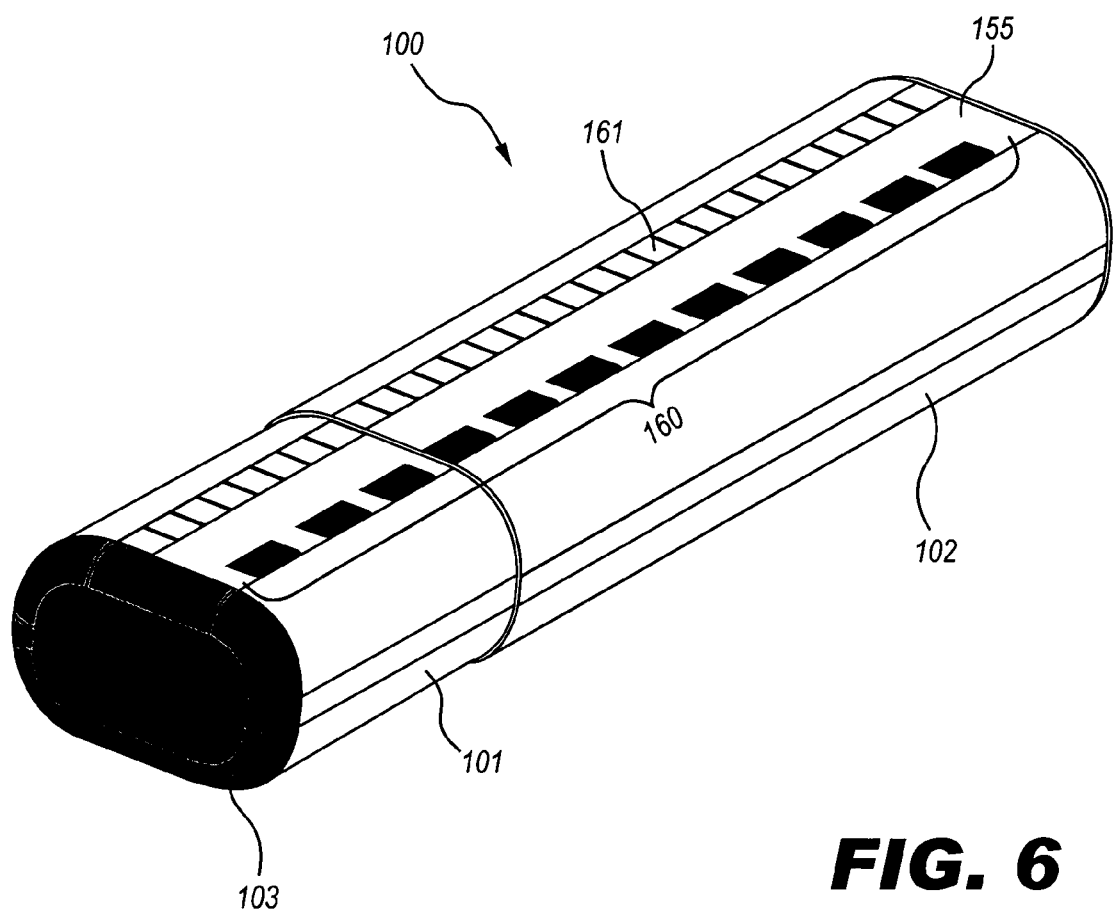
FIG. 6 is an assembled perspective view of the stimulator that illustrates a cathode array and anode extending along a portion of the first assembly according to principles described herein.

The anode (161) shown in FIGS. 5A and 5B may include a single, long, narrow electrode contact referred to herein and in the appended claims, unless otherwise specifically denoted, as a stripe electrode contact or a stripe anode. The anode (161) may alternatively include an array of individual electrode contacts, as illustrated in FIG. 5C. In some examples, the individual electrode contacts in the anode array (161) are electrically coupled with wires or other conductive mediums. Electrically coupled electrode contacts will be referred to herein and in the appended claims as "ganged." The individual electrode contacts may alternatively be individually controlled. Hence, although the following examples will be illustrated with stripe anodes, it will be recognized that the anodes may alternatively or additionally include individually controllable and/or ganged electrode contacts.

The array of cathodes (160) and/or the anode (161) shown in FIGS. 5A and 5B may extend along any portion of the stimulator (100). For example, the array of cathodes (160) and/or the anode (161) may extend along the length of the second assembly (102), as shown in FIG. 5A. However, as illustrated in the assembled perspective view of the stimulator (100) shown in FIG. 6, the cathode array (160) and/or the anode (161) may also extend along a portion of the first assembly (101). Hence, it will be recognized that the cathodes and/or anodes described in the examples given herein may extend along any portion of the stimulator (100).

Figure 7A:
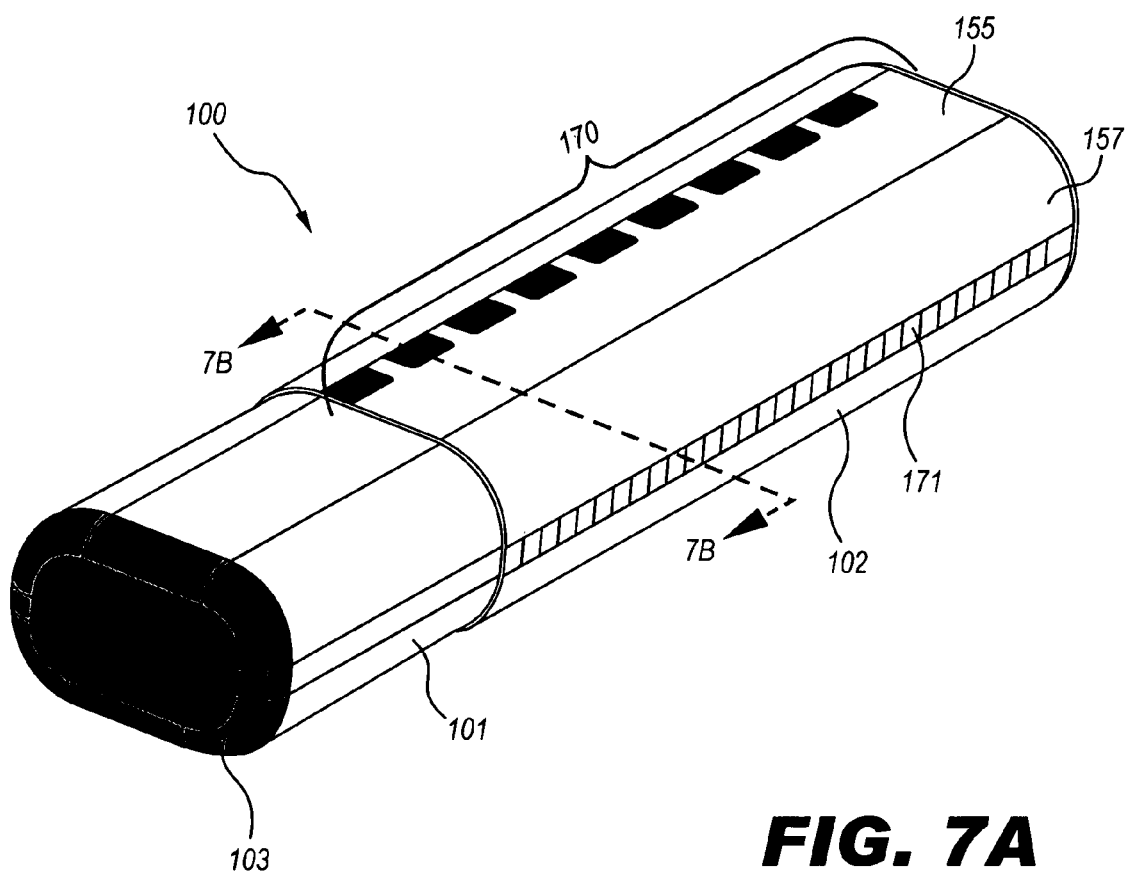
FIG. 7A is an assembled perspective view of the stimulator which illustrates another exemplary electrode contact arrangement that may be used to provide multipolar stimulation to a stimulation site according to principles described herein.
Figure 7B:
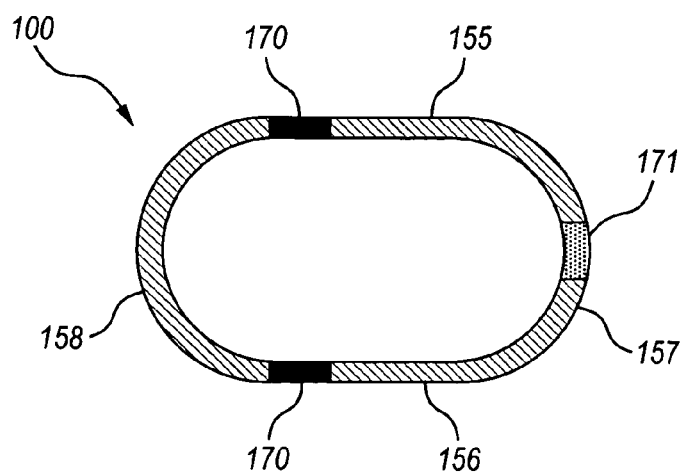
FIG. 7B is a cross-sectional view of the stimulator taken along the perspective line indicated in FIG. 7A according to principles described herein.

FIG. 7A is an assembled perspective view of the stimulator (100) which illustrates another exemplary electrode contact arrangement that may be used to provide multipolar stimulation to a stimulation site. As shown in FIG. 7A, an array of cathodes (170) similar to the array of cathodes (150) described in connection with FIG. 4A is located along the top surface (155) of the stimulator (100). Additionally or alternatively, as will be shown in FIG. 7B, the cathode array (170) may also be located along the bottom flat surface (156; FIG. 7B) of the stimulator (100). The stimulator (100) also includes an anodic electrode contact (anode) (171) located along the first rounded side surface (157). The anode (171) is similar to the anode (161) described in connection with FIG. 5A. A second anode (171) may additionally or alternatively be located along the second rounded side surface (158) of the stimulator (100), as will be described in more detail in connection with FIGS. 8A and 8B.

The array of cathodes (170) and/or the anode (171) illustrated in FIG. 7A may extend along any portion of the stimulator (100). For example, the array of cathodes (170) and/or the anode (171) may extend along the length of the second assembly (102), as shown in FIG. 7A. The cathode array (170) and/or the anode (171) may also extend along a portion of the first assembly (101).

FIG. 7B is a cross-sectional view of the stimulator (100) of FIG. 7A taken along the perspective line indicated in FIG. 7A that illustrates an exemplary location of the array of cathodes (170) and the anode (171). As shown in FIG. 7B, the cathode array (170) may be located along the top flat surface (155) and/or along the bottom flat surface (156) of the stimulator (100). The cathode arrays (170) are offset towards the second rounded side surface (158). However, it will be recognized that the cathode arrays (170) may be located along any portion of the top and bottom surfaces (155, 156).

The anode (171) is located along the first rounded side surface (157) and may be used with either of the cathode arrays (170). Hence, bipolar stimulation may be applied to a stimulation site on either the top or bottom sides (155, 156) of the stimulator (100).

Each of the electrode contacts in the cathode arrays (170) may be individually controlled. For example, one or more of the electrode contacts in the cathode array (170) may be designated as stimulating electrodes through which stimulation current is applied to one or more stimulation sites.

Moreover, one or more of the electrode contacts within the arrays of cathodes (170) may be configured to act as an anode. Hence, in some examples, one or more of the arrays of cathodes (170) may simultaneously include one or more electrodes acting as anodes and one or more electrodes acting as cathodes. Likewise, the anodic electrode contact (171) may be configured to act as a cathode. In this manner, any one or more of the electrode contacts located on the stimulator (100) may be used to stimulate one or more stimulation sites.

Figure 8A:
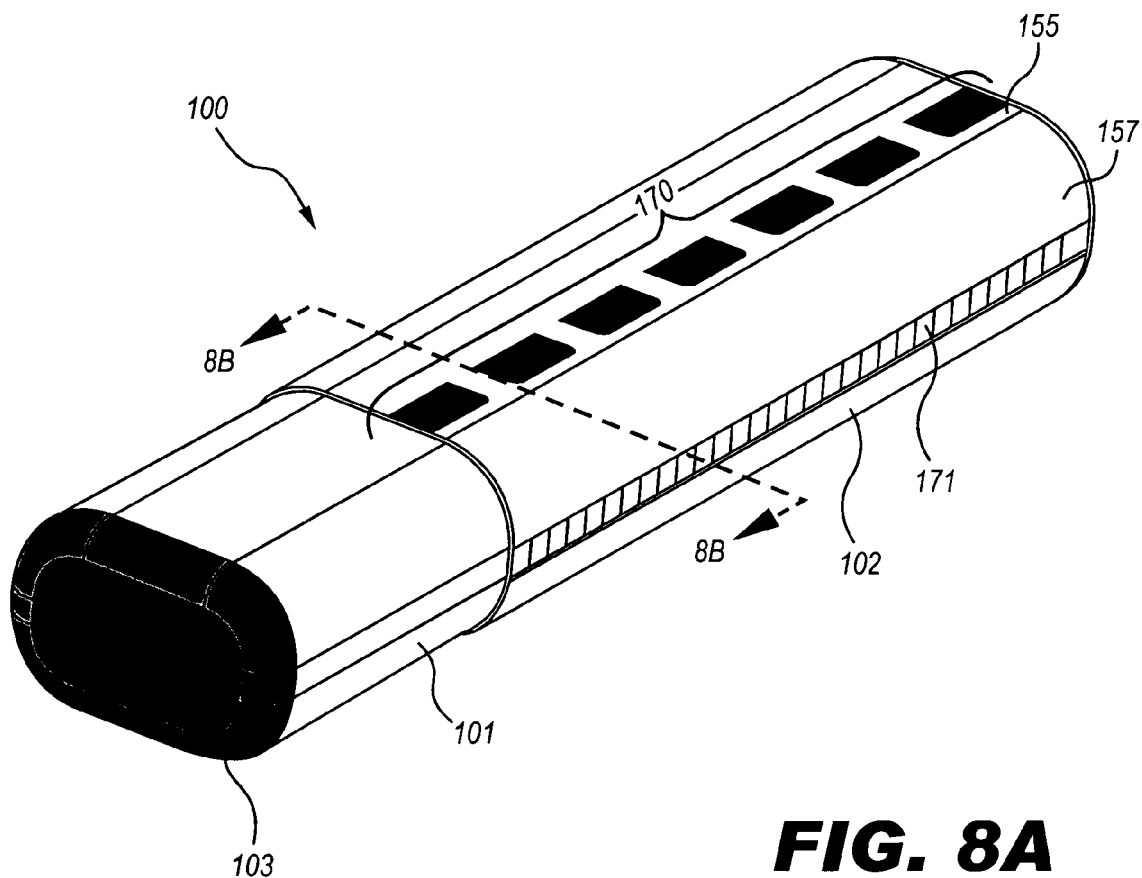
FIG. 8A is an assembled perspective view of the stimulator which illustrates another exemplary electrode contact arrangement that may be used to provide multipolar stimulation to a stimulation site according to principles described herein.
Figure 8B:
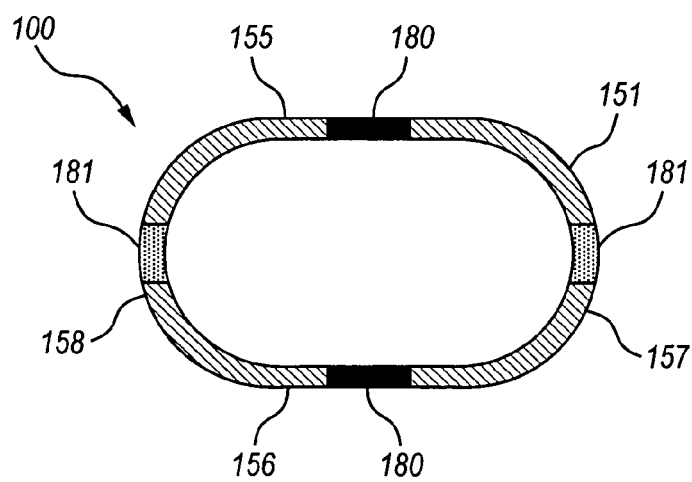
FIG. 8B is a cross-sectional view of the stimulator taken along the perspective line indicated in FIG. 8A according to principles described herein.

FIG. 8A is an assembled perspective view of the stimulator (100) which illustrates another exemplary electrode contact arrangement that may be used to provide multipolar stimulation to a stimulation site. As shown in FIG. 8A, an array of cathodes (180) similar to the array of cathodes (150) described in connection with FIG. 4A is located along the top surface (155) of the stimulator (100). Additionally or alternatively, as will be shown in FIG. 8B, the cathode array (180) may also be located along the bottom flat surface (156; FIG. 8B) of the stimulator (100). The stimulator (100) also includes an anodic electrode contact (anode) (181) located along the first rounded side surface (157). The anode (181) is similar to the anode (161) described in connection with FIG. 5A. A second anode (181), as will be shown in FIG. 8B, is also located along the second rounded side surface (158; FIG. 8B) of the stimulator (100).

The array of cathodes (180) and/or the anodes (181) may extend along any portion of the stimulator (100). For example, the array of cathodes (180) and/or the anodes (181) may extend along the length of the second assembly (102), as shown in FIG. 8A. The cathode array (180) and/or the anodes (181) may also extend along a portion of the first assembly (101).

FIG. 8B is a cross-sectional view of the stimulator (100) of FIG. 8A taken along the perspective line indicated in FIG. 8A that illustrates an exemplary location of the arrays of cathodes (180) and the anodes (181). As shown in FIG. 8B, the cathode arrays (180) may be located along the top flat surface (155) and/or along the bottom flat surface (156) of the stimulator (100). The cathode arrays (180) are centered along the width of the stimulator (100) for illustrative purposes only. However, it will be recognized that one or more of the arrays of cathodes (180) may be offset by any suitable distance from the center of the width of the stimulator (100) as best serves a particular application.

The anodes (181) are located along the first and second rounded side surfaces (157, 158) and may be used with either of the cathode arrays (180). Hence, in some examples, tripolar stimulation may be applied to a stimulation site with one of the cathode arrays (180) and both of the anodes (181). Tripolar stimulation may alternatively be applied to a stimulation site with one of the anodes (181) and both of the cathode arrays (180). Bipolar stimulation may alternatively be applied to a stimulation site with one of the anodes (181) and one of the arrays of cathodes (180).

Each of the electrode contacts in the cathode arrays (180) may be individually controlled. For example, one or more of the electrode contacts in the cathode arrays (180) may be designated as stimulating electrodes through which stimulation current is applied to one or more stimulation sites.

Moreover, one or more of the electrode contacts within the arrays of cathodes (180) may be configured to act as an anode. Hence, in some examples, one or more of the arrays of cathodes (180) may simultaneously include one or more electrodes acting as anodes and one or more electrodes acting as cathodes. Likewise, one or more of the anodic electrode contacts (181) may be configured to act as a cathode. In this manner, any one or more of the electrode contacts located on the stimulator (100) may be used to stimulate one or more stimulation sites.

Figure 9A:
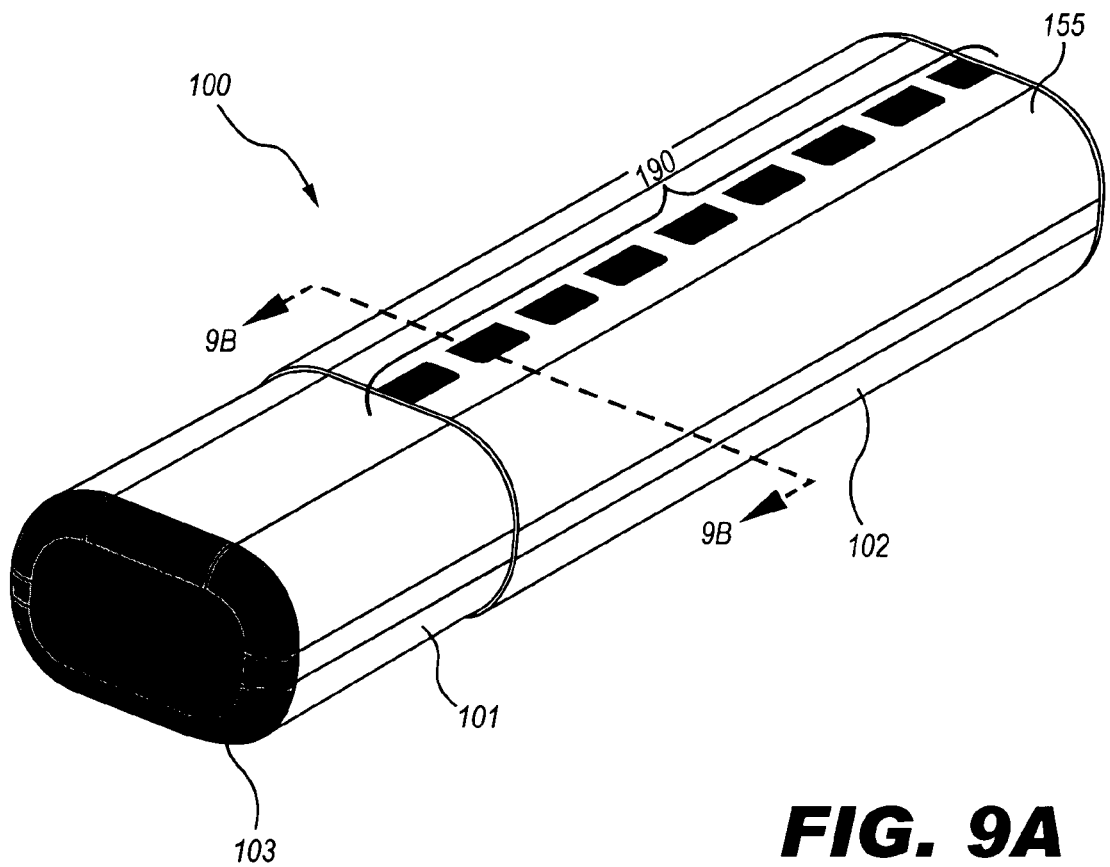
FIG. 9A is an assembled perspective view of the stimulator which illustrates another exemplary electrode contact arrangement that may be used to provide multipolar stimulation to a stimulation site according to principles described herein.
Figure 9B:
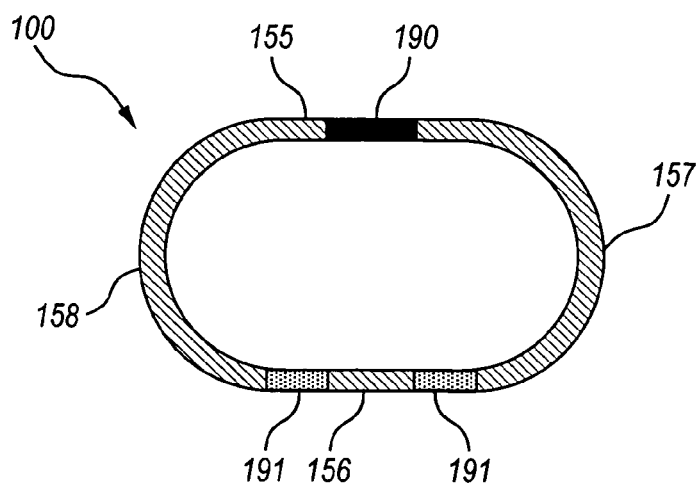
FIG. 9B is a cross-sectional view of the stimulator taken along the perspective line indicated in FIG. 9A according to principles described herein.

FIG. 9A is an assembled perspective view of the stimulator (100) which illustrates another exemplary electrode contact arrangement that may be used to provide multipolar stimulation to a stimulation site. As shown in FIG. 9A, an array of cathodes (190) similar to the array of cathodes (150) described in connection with FIG. 4A is located along the top surface (155) of the stimulator (100). The stimulator (100) also includes, as will be shown in FIG. 9B, two anodic electrode contacts (anodes) (191; FIG. 9B) along its bottom surface (156; FIG. 9B). The anodes (191) are similar to the anode (161) described in connection with FIG. 5A. It will be recognized that the cathode array (190) may alternatively be located along the bottom surface (156) and that the anodes (191; FIG. 9B) may alternatively be located long the top surface (155) of the stimulator (100).

The array of cathodes (190) and/or the anodes (191; FIG. 9B) may extend along any portion of the stimulator (100). For example, the array of cathodes (190) may extend along the length of the second assembly (102), as shown in FIG. 9A. The cathode array (190) and/or the anodes (191; FIG. 9B) may also extend along a portion of the first assembly (101).

FIG. 9B is a cross-sectional view of the stimulator (100) of FIG. 9A taken along the perspective line indicated in FIG. 9A that illustrates an exemplary location of the array of cathodes (190) and the anodes (191). As shown in FIG. 9B, the cathode array (190) is located along the top flat surface (155) of the stimulator (100) and the anodes (191) are located along the bottom flat surface (156) of the stimulator (100). The anodes (191) may additionally or alternatively be located along the first and/or second rounded side surfaces (157, 158). The cathode array (190) is centered along the width of the stimulator (100) for illustrative purposes only. However, it will be recognized that the cathode array (190) may be offset by any suitable distance in either direction from the center of the width of the stimulator (100) as best serves a particular application. Likewise, the anodes (191) illustrated in FIG. 9B may be separated by any suitable distance along the width of the bottom surface (156) of the stimulator (100).

In some examples, the array of cathodes (190) and the anodes (191) are symmetrically arranged. In other words, the array of cathodes (190) is laterally centered in between the anodes (191), as shown in FIG. 9B. Such a symmetric arrangement may be advantageous in some tripolar stimulation configurations. However, in some alternative examples, the array of cathodes (190) and the anodes (191) are asymmetrically arranged.

The anode (191) and cathode (190) configuration of FIG. 9B may be used to apply tripolar stimulation to a stimulation site and allows the stimulation current to remain predominately on the side of the stimulator (100) that includes the array of cathodes (190). In some examples, the configuration of FIG. 9B may excite a larger area than the configuration of FIG. 8B because of the distance of separation between the anodes (191) and the array of cathodes (191) in FIG. 9B. Bipolar stimulation may alternatively be applied to a stimulation site by switching off one of the anodes (191). The asymmetrical arrangement of the electrode arrays of FIG. 9B is particularly suitable for enabling multiple possible separation distances between the anodes (191) and array of cathodes (190).

Each of the electrode contacts in the cathode array (190) may be individually controlled. For example, one or more of the electrode contacts in the cathode array (190) may be designated as stimulating electrodes through which stimulation current is applied to one or more stimulation sites.

Moreover, one or more of the electrode contacts within the array of cathodes (190) may be configured to act as an anode. Hence, in some examples, the array of cathodes (190) may simultaneously include one or more electrodes acting as anodes and one or more electrodes acting as cathodes. Likewise, one or more of the anodic electrode contacts (191) may be configured to act as a cathode. In this manner, any one or more of the electrode contacts located on the stimulator (100) may be used to stimulate one or more stimulation sites.

Figure 10A:
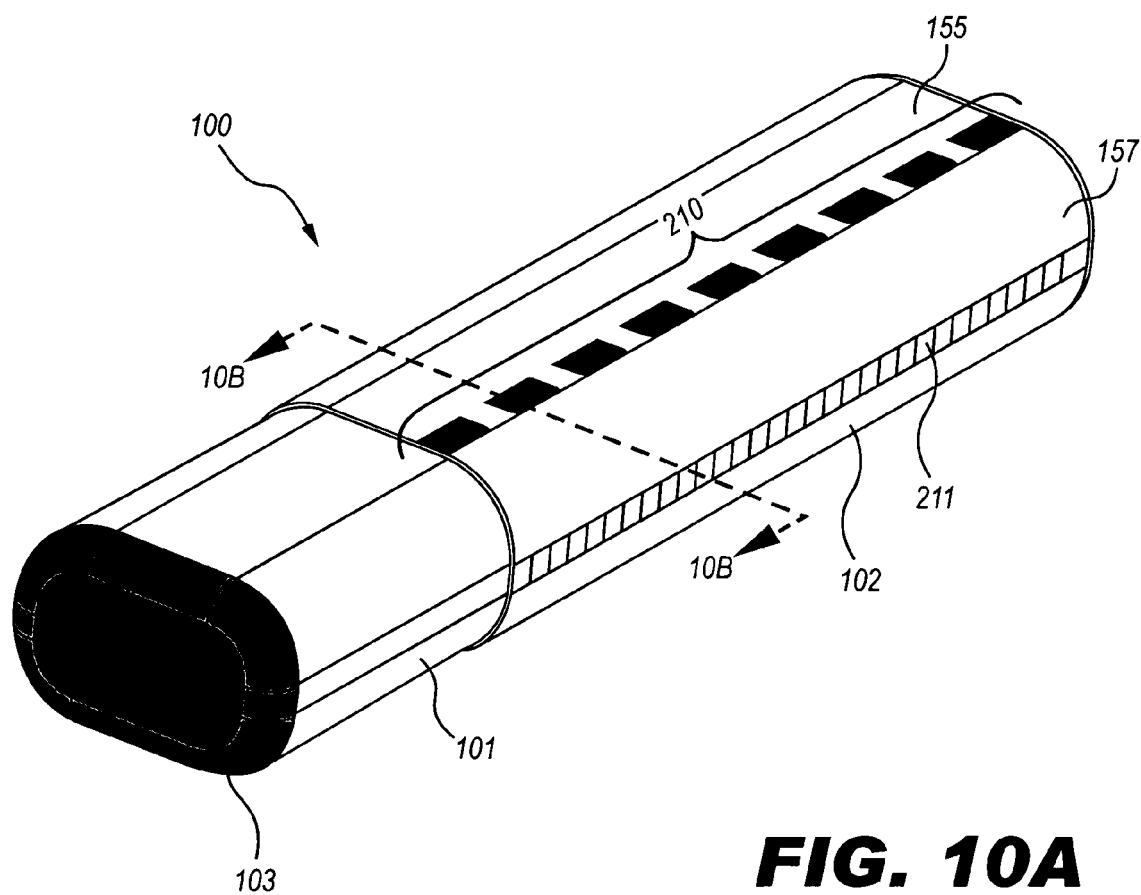
FIG. 10A is an assembled perspective view of the stimulator which illustrates another exemplary electrode contact arrangement that may be used to provide multipolar stimulation to a stimulation site according to principles described herein.
Figure 10B:
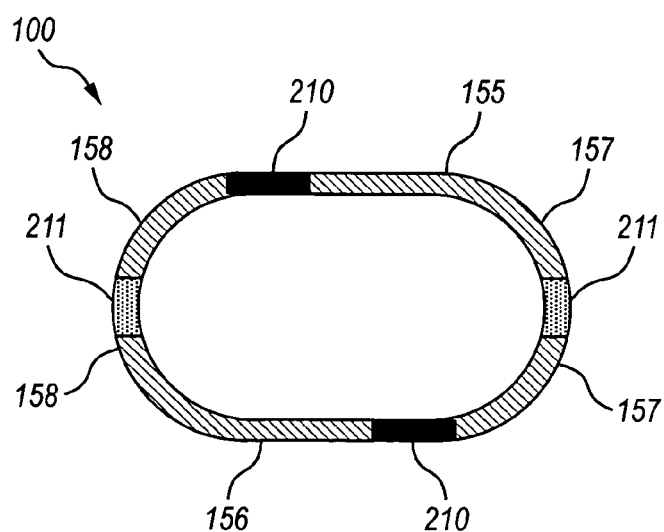
FIG. 10B is a cross-sectional view of the stimulator taken along the perspective line indicated in FIG. 10A according to principles described herein.

FIG. 10A is an assembled perspective view of the stimulator (100) which illustrates another exemplary electrode contact arrangement that may be used to provide multipolar stimulation to a stimulation site. As shown in FIG. 10A, an array of cathodes (210) similar to the array of cathodes (150) described in connection with FIG. 4A is located along the top surface (155) of the stimulator (100). Additionally or alternatively, as will be shown in FIG. 10B, the cathode array (210) may also be located along the bottom flat surface (156; FIG. 10B) of the stimulator (100). The stimulator (100) also includes an anodic electrode contact (anode) (211) located along the first rounded side surface (157). The anode (211) is similar to the anode (161) described in connection with FIG. 5A. A second anode (211), as will be shown in FIG. 10B, may also be located along the second rounded side surface (158; FIG. 10B) of the stimulator (100).

The array of cathodes (210) and/or the anodes (211) may extend along any portion of the stimulator (100). For example, the array of cathodes (210) and/or the anodes (211) may extend along the length of the second assembly (102), as shown in FIG. 10A. The cathode array (210) and/or the anodes (211) may also extend along a portion of the first assembly (101).

FIG. 10B is a cross-sectional view of the stimulator (100) of FIG. 10A taken along the perspective line indicated in FIG. 10A that illustrates an exemplary location of the arrays of cathodes (210) and the anodes (211). As shown in FIG. 10B, the cathode arrays (210) may be located along the top flat surface (155) and along the bottom flat surface (156) of the stimulator (100). One of the cathode arrays (210) is offset towards the first rounded side surface (157) and one of the cathode arrays (210) is offset towards the second rounded side surface (158). However, it will be recognized that the cathode arrays (210) may be located along any portion of the top and bottom surfaces (155, 156) as best serves a particular application.

The anodes (211) are located along the first and second rounded side surfaces (157, 158) and may be used with either of the cathode arrays (210). Hence, in some examples, tripolar stimulation may be applied to a stimulation site with one of the cathode arrays (210) and both of the anodes (211). Tripolar stimulation may alternatively be applied to a stimulation site with one of the anodes (211) and both of the cathode arrays (210). Bipolar stimulation may alternatively be applied to a stimulation site with one of the anodes (211) and one of the arrays of cathodes (210). Moreover, in this exemplary arrangement, multiple distances between the anodes (211) and arrays of cathodes (210) are achievable.

Each of the electrode contacts in the cathode arrays (210) may be individually controlled. For example, one or more of the electrode contacts in the cathode arrays (210) may be designated as stimulating electrodes through which stimulation current is applied to one or more stimulation sites.

Moreover, one or more of the electrode contacts within the arrays of cathodes (210) may be configured to act as an anode. Hence, in some examples, one or more of the arrays of cathodes (210) may simultaneously include one or more electrodes acting as anodes and one or more electrodes acting as cathodes. Likewise, one or more of the anodic electrode contacts (211) may be configured to act as a cathode. In this manner, any one or more of the electrode contacts located on the stimulator (100) may be used to stimulate one or more stimulation sites.

Figure 11A:
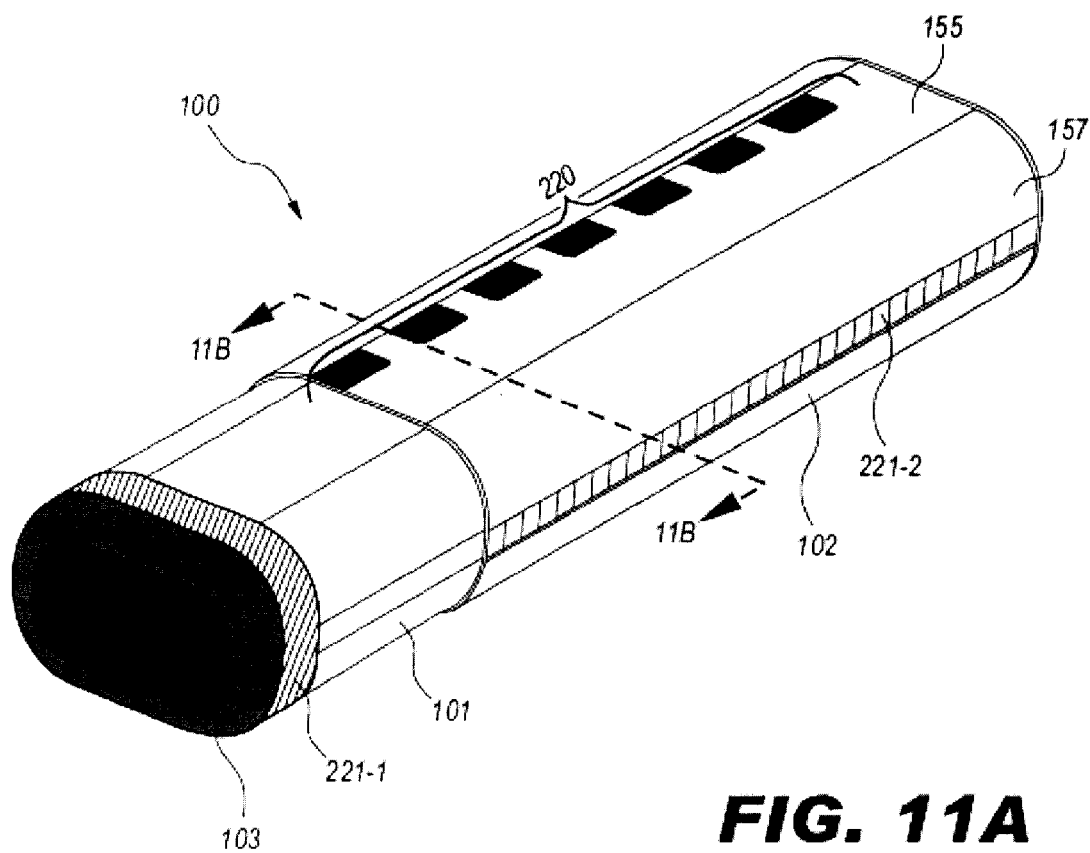
FIG. 11A is an assembled perspective view of the stimulator which illustrates another exemplary electrode contact arrangement that may be used to provide monopolar and/or multipolar stimulation to a stimulation site according to principles described herein.
Figure 11B:
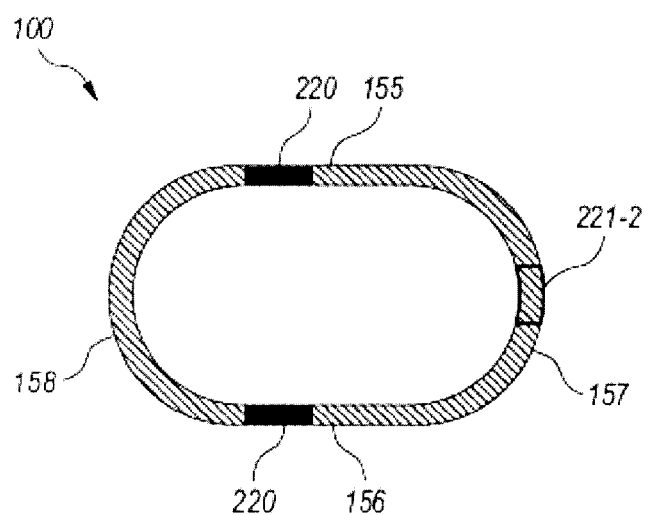
FIG. 11B is a cross-sectional view of the stimulator taken along the perspective line indicated in FIG. 11A according to principles described herein.

FIG. 11A is an assembled perspective view of the stimulator (100) which illustrates another exemplary electrode contact arrangement that may be used to provide monopolar and/or multipolar stimulation to a stimulation site. FIG. 11B is a cross-sectional view of the stimulator (100) taken along the perspective line indicated in FIG. 11A. As illustrated in FIGS. 11A and 11B, the electrode contact arrangement is similar to that described in connection with FIGS. 7A and 7B with the addition of an anode (221-1) that surrounds a portion, or all, of the perimeter of the stimulator (100). Hence, as shown in FIG. 11B, a cathode array (220) is located along the top flat surface (155) and/or along the bottom flat surface (156) of the stimulator (100). The cathode arrays (220) are offset towards the second rounded side surface (158). However, it will be recognized that the cathode arrays (220) may be located along any portion of the top and bottom surfaces (155, 156).

An anode (221-2), which may be a stripe electrode contact or a ganged electrode contact, is located along the first rounded side surface (157) and may be used with either of the cathode arrays (220). Hence, bipolar stimulation may be applied to a stimulation site on either the top or bottom sides (155, 156) of the stimulator (100). In addition, the anode (221-1) surrounds a portion, or all, of the perimeter of the stimulator (100).

Each anode (221-1, 221-2) may be selectively switched on or off so that the stimulator (100) may deliver monopolar or bipolar stimulation to a stimulation site. For example, the anode (221-1) maybe switched off when it is desired to deliver bipolar stimulation to a stimulation site. Likewise, the anode (221-2) may be switched off when it is desired to deliver monopolar stimulation to a stimulation site.

Each of the electrode contacts in the cathode arrays (220) may be individually controlled. For example, one or more of the electrode contacts in the cathode array (220) may be designated as stimulating electrodes through which stimulation current is applied to one or more stimulation sites.

Moreover, one or more of the electrode contacts within the arrays of cathodes (220) may be configured to act as an anode. Hence, in some examples, one or more of the arrays of cathodes (220) may simultaneously include one or more electrodes acting as anodes and one or more electrodes acting as cathodes. Likewise, the anodic electrode contacts (221-1, 221-2) may be configured to act as a cathode. In this manner, any one or more of the electrode contacts located on the stimulator (100) may be used to stimulate one or more stimulation sites.

Figure 12A:
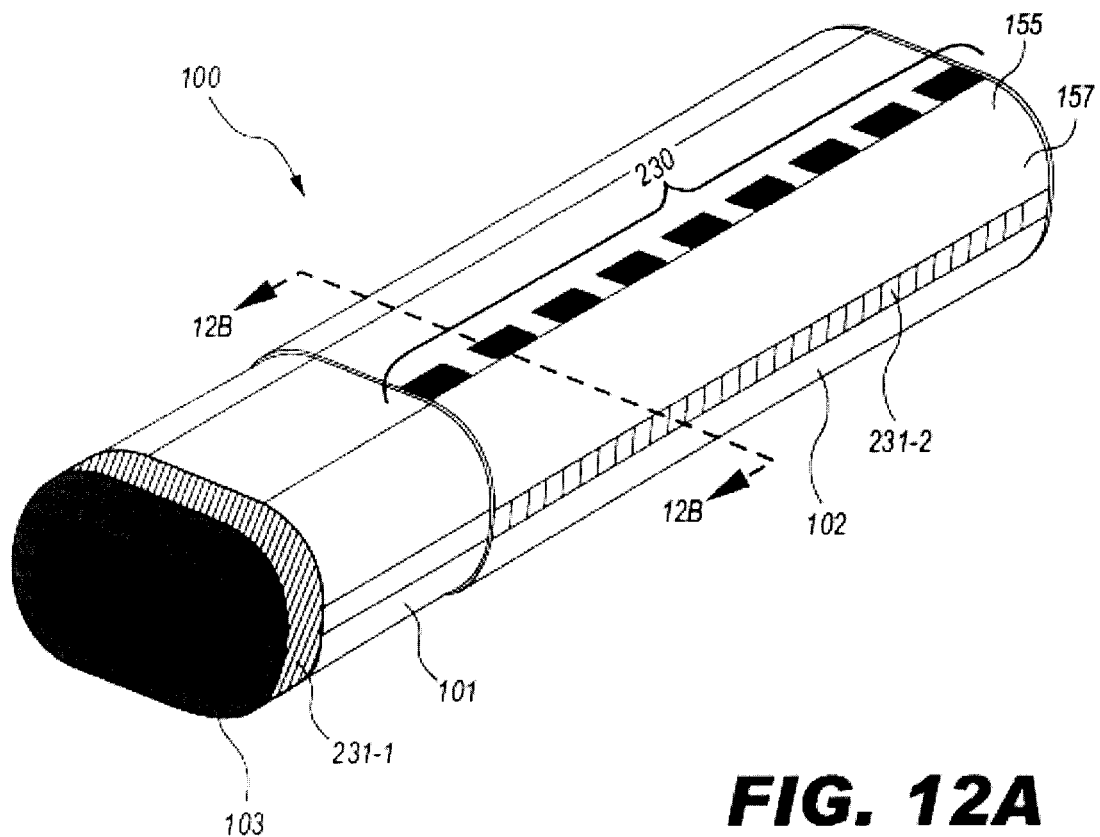
FIG. 12A is an assembled perspective view of the stimulator which illustrates another exemplary electrode contact arrangement that may be used to provide monopolar and/or multipolar stimulation to a stimulation site according to principles described herein.
Figure 12B:
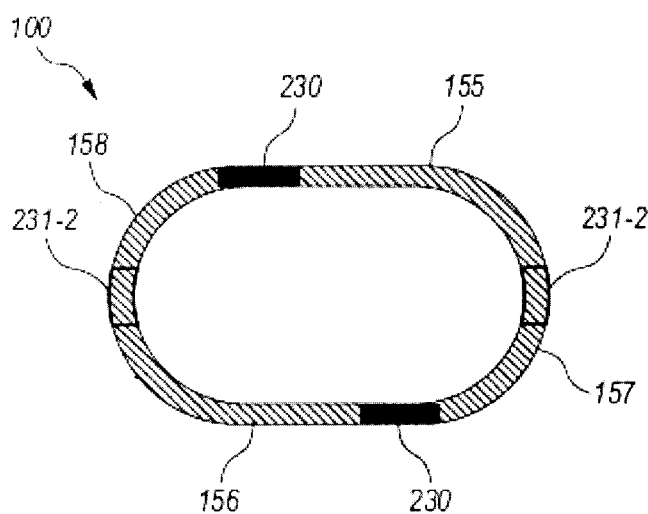
FIG. 12B is a cross-sectional view of the stimulator taken along the perspective line indicated in FIG. 12A according to principles described herein.

FIG. 12A is an assembled perspective view of the stimulator (100) which illustrates another exemplary electrode contact arrangement that may be used to provide monopolar and/or multipolar stimulation to a stimulation site. FIG. 12B is a cross-sectional view of the stimulator (100) taken along the perspective line indicated in FIG. 12A. As illustrated in FIGS. 12A and 12B, the electrode contact arrangement is similar to that described in connection with FIGS. 10A and 10B with the addition of an anode (231-1) that surrounds a portion, or all, of the perimeter of the stimulator (100). Hence, as shown in FIG. 12B, a cathode array (230) is located along the top flat surface (155) and along the bottom flat surface (156) of the stimulator (100). One of the cathode arrays (230) is offset towards the first rounded side surface (157) and one of the cathode arrays (230) is offset towards the second rounded side surface (158). However, it will be recognized that the cathode arrays (230) may be located along any portion of the top and bottom surfaces (155, 156) as best serves a particular application.

An anode (231-2), which may be a stripe electrode contact or a ganged electrode contact, is located along the first and second rounded side surfaces (157, 158) and may be used with either of the cathode arrays (230). In addition, as shown in FIG. 12B, the anode (231-1) surrounds a portion, or all, of the perimeter of the stimulator (100).

Each anode (231-1, 231-2) may be selectively switched on or off so that the stimulator (100) may deliver monopolar, bipolar, or tripolar stimulation to a stimulation site. For example, the anode (231-1) may be switched off when it is desired to deliver tripolar stimulation to a stimulation site. Likewise, the anode (231-1) and one of the anodes (231-2) may be switched off when it is desired to deliver bipolar stimulation to a stimulation site. Finally, both of the anodes (231-2) may be switched off when it is desired to deliver monopolar stimulation to a stimulation site.

Each of the electrode contacts in the cathode arrays (230) may be individually controlled. For example, one or more of the electrode contacts in the cathode array (230) may be designated as stimulating electrodes through which stimulation current is applied to one or more stimulation sites.

Moreover, one or more of the electrode contacts within the arrays of cathodes (230) may be configured to act as an anode. Hence, in some examples, one or more of the arrays of cathodes (230) may simultaneously include one or more electrodes acting as anodes and one or more electrodes acting as cathodes. Likewise, the anodic electrode contacts (231-1, 231-2) may be configured to act as a cathode. In this manner, any one or more of the electrode contacts located on the stimulator (100) may be used to stimulate one or more stimulation sites.

Figure 13:
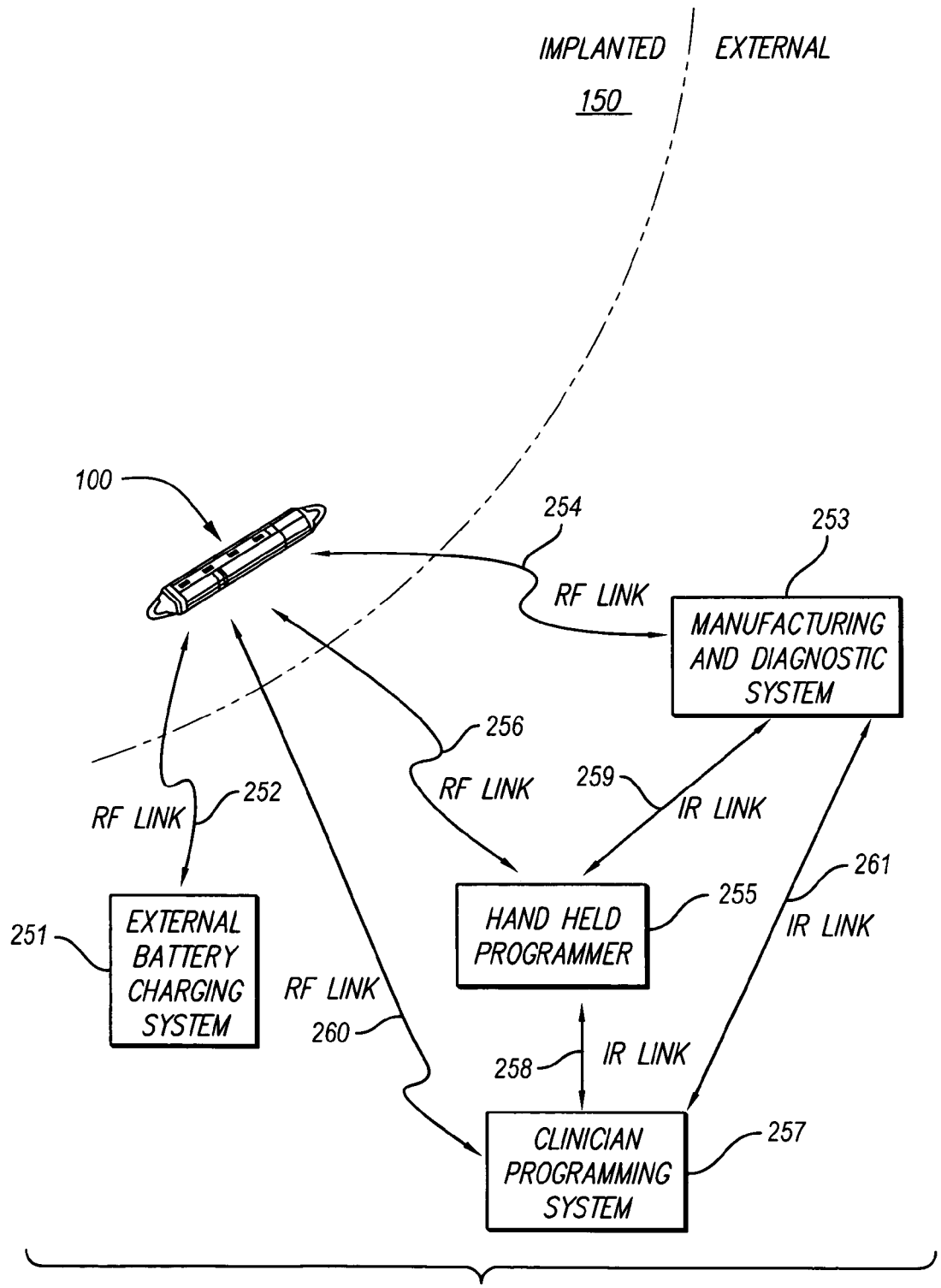
FIG. 13 illustrates various systems and external devices that may be used to support the implanted stimulator according to principles described herein.

FIG. 13 illustrates an exemplary implanted stimulator (100) and examples of the various systems and external devices that may be used communicate with and/or transfer power to the stimulator (100). For example, an external battery charging system (EBCS) (251) may provide power used to recharge the power source (145; FIG. 1) via an RF link (252). External devices including, but not limited to, a hand held programmer (HHP) (255), clinician programming system (CPS) (257), and/or a manufacturing and diagnostic system (MDS) (253) may be configured to activate, deactivate, program, and test the stimulator (100) via one or more RF links (254, 256). It will be recognized that the RF links (252, 254, 256) may be any type of link such as an optical link, a thermal link, or any other energy-coupling link.

Additionally, if multiple external devices are used in the treatment of a patient, there may be some communication among those external devices, as well as with the implanted stimulator (100). For example, the CPS (257) may communicate with the HHP (255) via an infrared (IR) link (258), with the MDS (253) via an IR link (261), and/or directly with the stimulator (100) via an RF link (260). These communication links (258, 261, 260) are not limited to IR and RF links and may include any other type of communication link. Likewise, the MDS (253) may communicate with the HHP (255) via an IR link (259) or via any other suitable communication link.

The HHP (255), MDS (253), CPS (257), and EBCS (251) are merely illustrative of the many different external devices that may be used in connection with the stimulator (100). Furthermore, it will be recognized that the functions performed by any two or more of the HHP (255), MDS (253), CPS (257), and EBCS (251) may be performed by a single external device. One or more of the external devices (253, 255, 257) may be embedded in a seat cushion, mattress cover, pillow, garment, belt, strap, pouch, or the like so as to be positioned near the implanted stimulator (100) when in use.

The stimulator (100) of FIG. 13 may be configured to operate independently. Alternatively, as will be described in more detail below, the stimulator (100) may be configured to operate in a coordinated manner with one or more additional stimulators, other implanted devices, or other devices external to the patient's body.

To determine the strength and/or duration of electrical stimulation required to most effectively treat a particular medical condition, various indicators of the medical condition and/or a patient's response to treatment may be sensed or measured. These indicators include, but are not limited to, muscle or limb activity (e.g., electromyography (EMG)), electrical activity of the brain (e.g., EEG), neurotransmitter levels, hormone levels, and/or medication levels. In some embodiments, the stimulator (100) may be configured to change the stimulation parameters in a closed loop manner in response to these measurements. The stimulator (100) may be configured to perform the measurements. Alternatively, other sensing devices may be configured to perform the measurements and transmit the measured values to the stimulator (100).

Thus, it is seen that one or more external appliances may be provided to interact with the stimulator (100), and may be used to accomplish at least one or more of the following functions:

Function 1: If necessary, transmit electrical power to the stimulator (100) in order to power the stimulator (100) and/or recharge the power source (145, FIG. 1).

Function 2: Transmit data to the stimulator (100) in order to change the stimulation parameters used by the stimulator (100).

Function 3: Receive data indicating the state of the stimulator (100) (e.g., battery level, stimulation parameters, etc.).

Additional functions may include adjusting the stimulation parameters based on information sensed by the stimulator (100) or by other sensing devices.

By way of example, an exemplary method of treating a particular medical condition within a patient may be carried out according to the following sequence of procedures. The steps listed below may be modified, reordered, and/or added to as best serves a particular application.

1. A stimulator (100) is implanted so that one or more of its electrode contacts described in connection with FIGS. 4A-12B are coupled to or located near a stimulation site.

2. The stimulator (100) is programmed to apply electrical stimulation to the stimulation site.

3. When the patient desires to invoke stimulation, the patient sends a command to the stimulator (100) (e.g., via a remote control) such that the stimulator (100) delivers the prescribed stimulation. The stimulator (100) may be alternatively or additionally configured to automatically apply the stimulation in response to sensed indicators of a particular medical condition.

4. To cease stimulation, the patient may turn off the stimulator (100) (e.g., via a remote control).

5. Periodically, the power source (145, FIG. 1) of the stimulator (100) is recharged, if necessary, in accordance with Function 1 described above.

For the treatment of any of the various types of medical conditions, it may be desirable to modify or adjust the algorithmic functions performed by the implanted and/or external components, as well as the surgical approaches. For example, in some situations, it may be desirable to employ more than one stimulator (100), each of which could be separately controlled by means of a digital address. Multiple channels and/or multiple patterns of electrical may thereby be used to treat multiple medical conditions.

Figure 14:
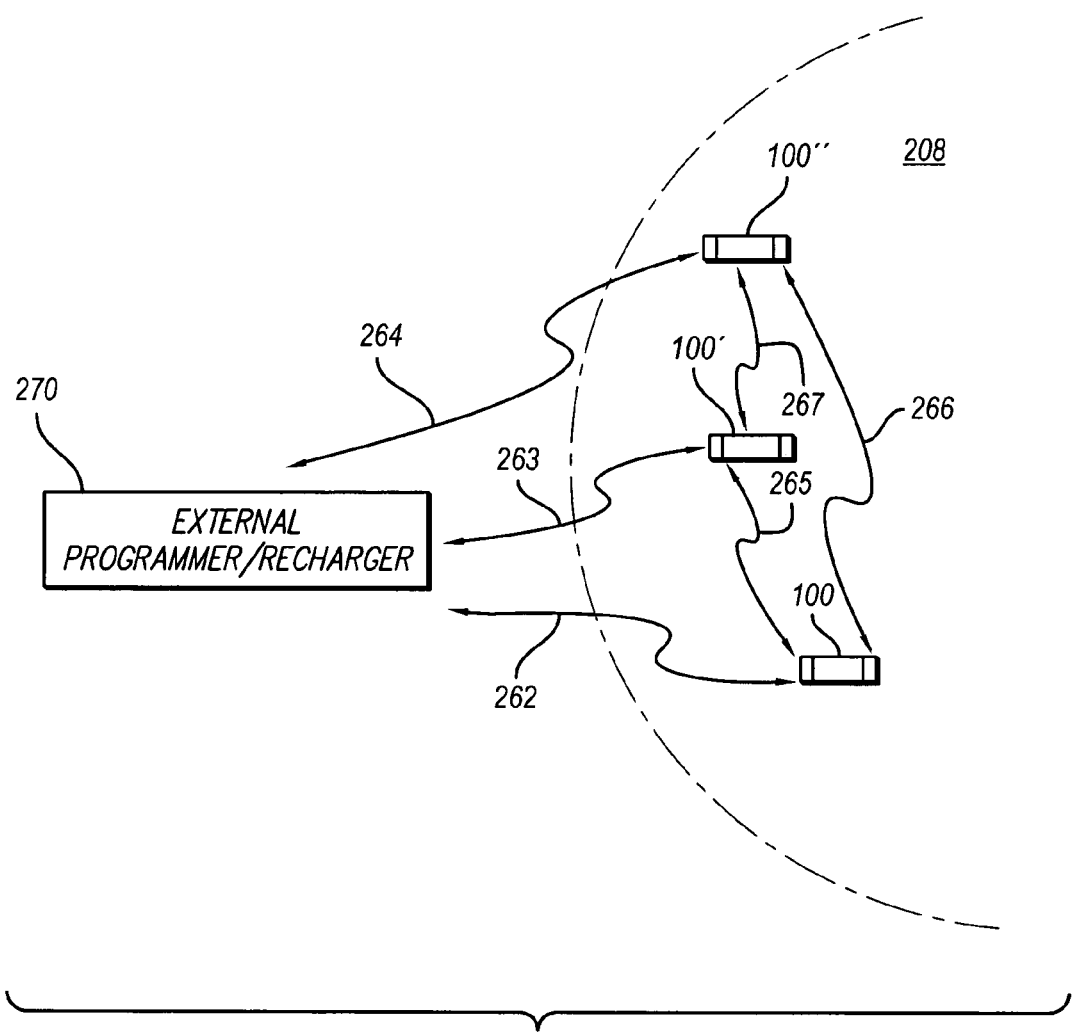
FIG. 14 depicts a number of stimulators configured to communicate with each other and/or with one or more external devices according to principles described herein.

For instance, as shown in the example of FIG. 14, a first stimulator (100) implanted beneath the skin (208) of the patient provides a stimulus to a first location; a second stimulator (100') provides a stimulus to a second location; and a third stimulator (100") provides a stimulus to a third location. As previously mentioned, the implanted devices may operate independently or may operate in a coordinated manner with other implanted devices or other devices external to the patient's body. That is, an external controller (270) may be configured to control the operation of each of the implanted devices (100, 100', and 100"). In some embodiments, an implanted device, e.g. stimulator (100), may control or operate under the control of another implanted device(s), e.g. stimulator (100') and/or stimulator (100"). Control lines (262-267) have been drawn in FIG. 14 to illustrate that the external controller (270) may communicate or provide power to any of the implanted devices (100, 100', and 100") and that each of the various implanted devices (100, 100', and 100") may communicate with and, in some instances, control any of the other implanted devices.

As a further example of multiple stimulators (100) operating in a coordinated manner, the first and second stimulators (100, 100') of FIG. 14 may be configured to sense various indicators of a particular medical condition and transmit the measured information to the third stimulator (100"). The third stimulator (100") may then use the measured information to adjust its stimulation parameters and apply electrical stimulation to a stimulation site accordingly.

Alternatively, the external device (250) or other external devices communicating with the external device may be configured to sense various indicators of a patient's condition. The sensed indicators can then be transmitted to the external device (250) or to one or more of the implanted stimulators which may adjust stimulation parameters accordingly. In other examples, the external controller (270) may determine whether any change to stimulation parameters is needed based on the sensed indicators. The external device (250) may then signal a command to one or more of the stimulators to adjust stimulation parameters accordingly.

Figure 15:
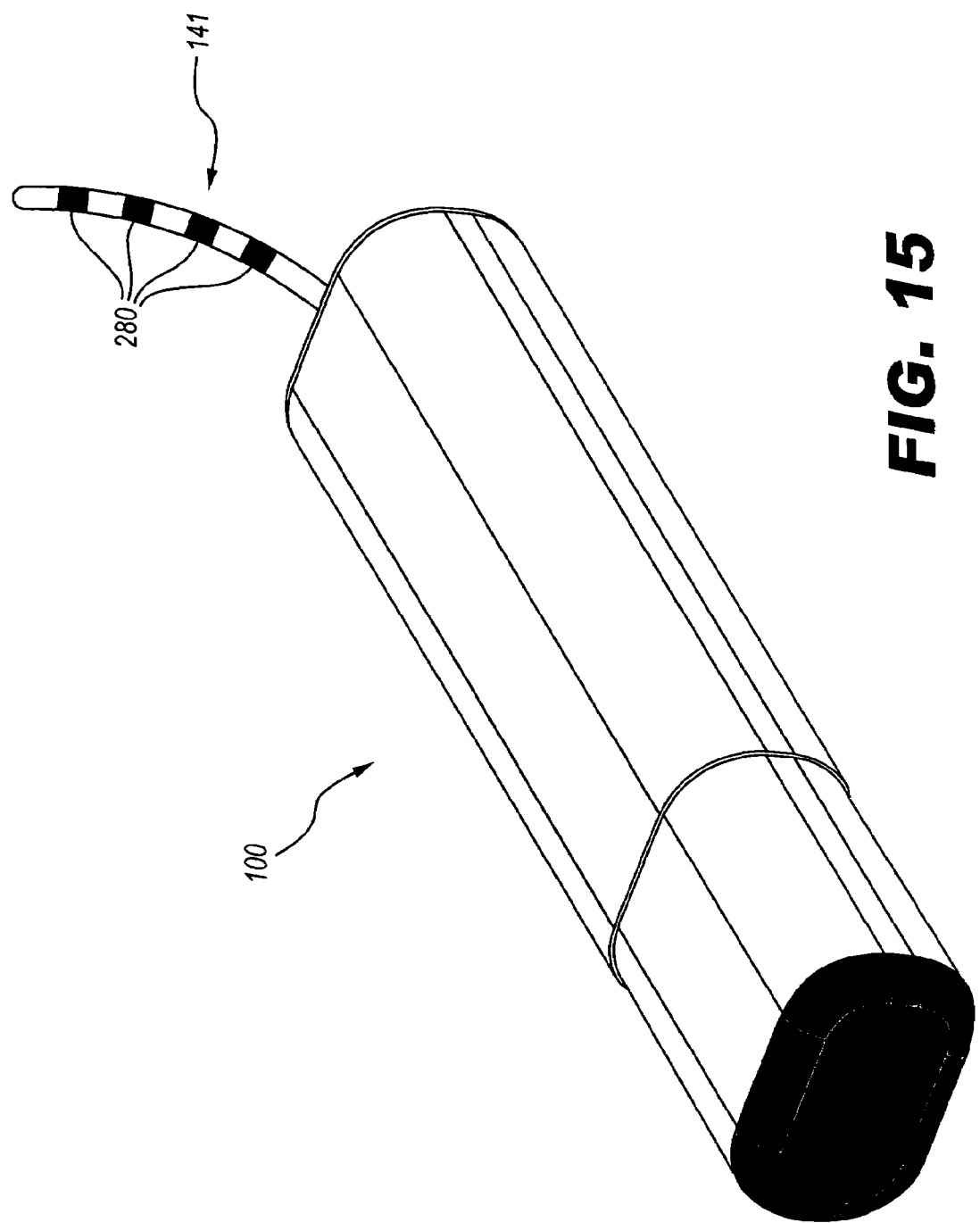
FIG. 15 illustrates a stimulator coupled to an exemplary lead having a number of electrode contacts disposed thereon according to principles described herein.

As mentioned previously and as illustrated in FIG. 15, the stimulator (100) may be coupled to a lead (141) having a number of electrode contacts (280) disposed thereon. The lead (141) may be of any suitable length and include any number of electrode contacts (280). Each of the electrode contacts (280) may be selectively configured to act as anodes and/or cathodes. In some examples, one or more of the electrode contacts (280) may be configured to act as an anode for a corresponding cathode disposed on the body of the stimulator (280). Such a configuration may be used to provide a more monopolar stimulation to the stimulation site. It will be recognized that the lead (141) shown in FIG. 15 may be coupled to any of the exemplary stimulators (100) described herein.

The stimulator (100) described herein may be used in the treatment of a wide variety of different medical, psychiatric, and neurological conditions and/or disorders. A number of these conditions and disorders will now be described below. However, it will be understood that this description is merely exemplary and is not limiting in any way. The stimulator (100) described herein may be used to treat any condition or disorder where stimulation from an implanted stimulator is helpful to treat the symptoms or cause of the condition or disorder.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A device comprising:
an implantable stimulator configured and arranged for stimulation of a nerve and for implantation into tissue of a patient near the nerve, said stimulator comprising
electrical circuitry configured to produce an electrical stimulation pulse,
a power source configured and arranged to supply the electrical circuitry with power,
a housing that houses the electrical circuitry and the power source, wherein the housing comprises a substantially flat first external surface, a substantially flat second external surface that is opposite the first external surface, a substantially rounded third external surface and a substantially rounded fourth external surface, wherein the third and fourth external surfaces couple the first external surface to the second external surface, and wherein the substantially flat first external surface is a top surface and the substantially flat second external surface is a bottom surface;
at least one electrode contact array comprising multiple electrode contacts disposed on the first external surface of said housing of said stimulator, and
at least one additional electrode contact disposed, at least in part, on the second external surface or the third external surface of said housing.

2. The device of claim 1, wherein said electrode contacts in said electrode contact array are arranged in a single row that extends along a portion of a length of said housing of said stimulator.

3. The device of claim 1, wherein said at least one additional electrode contact comprises a ring electrode contact that is disposed around a circumference of said housing of said stimulator on a portion of each of the first, second, third and fourth external surfaces.

4. The device of claim 1, wherein said at least one additional electrode contact comprises a stripe electrode that extends along a portion of a length of said housing of said stimulator.

5. The device of claim 1, wherein said at least one additional electrode contact comprises an array of individual electrode contacts.

6. The device of claim 5, wherein said individual electrode contacts are ganged.

7. The device of claim 1, wherein said at least one electrode contact array comprises a first electrode contact array disposed on said substantially flat first external surface and wherein said at least one additional electrode contact comprises a second electrode contact array disposed on said substantially flat second external surface.

8. The device of claim 7, wherein said first and second electrode contact arrays are centered with reference to a width of said housing of said stimulator.

9. The device of claim 7, wherein said first and second electrode contact arrays are offset from a center of a width of said housing of said stimulator.

10. The device of claim 7, further comprising a ring electrode contact that is disposed around a circumference of said housing of said stimulator on a portion of each of the first, second, third and fourth external surfaces.

11. The device of claim 1, wherein said at least one electrode contact array comprises a first electrode contact array disposed on said substantially flat first external surface and said at least one additional electrode contact is disposed on said substantially rounded third external surface.

12. The device of claim 11, further comprising at least one electrode contact disposed on the substantially rounded fourth external surface.

13. The device of claim 1, further comprising one or more electrode contacts disposed on the substantially rounded third external surface, wherein:
said at least one electrode contact array comprises a first electrode contact array disposed on said substantially flat first external surface; and
said at least one additional electrode contact comprises one or more electrode contacts disposed on said substantially flat second external surface.

14. The device of claim 13, further comprising one or more electrode contacts disposed on the substantially rounded fourth external surface of the housing.

15. The device of claim 1, further comprising a cap assembly disposed on an end portion of said housing of said stimulator, wherein said at least one additional electrode contact is disposed on said cap assembly.

16. The device of claim 1, wherein the housing comprises
a first housing assembly that houses a power source and a second housing assembly that houses electrical circuitry configured to produce an electrical stimulation pulse, wherein the power source is configured and arranged to supply the electrical circuitry with power.

17. The device of claim 16, wherein the stimulator further comprises a cap assembly that caps an end of the housing.

18. The device of claim 16, wherein the at least one additional electrode contact comprises a ring electrode contact that is disposed around a circumference of the housing on a portion of each of the first, second, third and fourth external surfaces.

19. The device of claim 16, wherein:
the first housing assembly is elongate; and
the multiple electrode contacts of the at least one electrode contact array are disposed in a longitudinal row along an external surface of the first housing assembly.

20. The device of claim 16, wherein an external surface of the second housing assembly is free of the multiple electrode contacts of the at least one electrode contact array.

21. The device of claim 1, wherein said at least one electrode contact array comprises a first electrode contact array disposed on the substantially flat first external surface of the housing and wherein said at least one additional electrode contact comprises a second electrode contact array and a third electrode contact array disposed on the substantially flat second external surface of the housing.

22. The device of claim 20, wherein an external surface of the second housing assembly is free of the at least one additional electrode contact.

23. The device of claim 21, further comprising at least one electrode contact disposed on the substantially rounded third external surface of said housing of said stimulator.

24. The device of claim 1, wherein said at least one electrode contact array comprises a first electrode contact array and a second electrode contact array disposed on the substantially flat first external surface of the housing and wherein said at least one additional electrode contact comprises a third electrode contact array and a fourth electrode contact array disposed on the substantially flat second external surface of the housing.

25. The device of claim 1, further comprising at least one electrode contact array disposed on said substantially rounded third external surface, wherein said at least one electrode contact array comprises a first electrode contact array disposed on said substantially flat first external surface, wherein said at least one additional electrode contact comprises a second electrode contact array disposed on said substantially flat second external surface, and wherein said first electrode array and said second electrode array are offset from a center of a width of said housing of said stimulator.

26. The device of claim 25, further comprising at least one electrode contact disposed on said substantially rounded fourth external surface.

27. A method of stimulating a stimulation site within a patient, said method comprising:
providing a stimulator comprising at least one electrode contact array, said array comprising multiple electrode contacts disposed on a substantially flat first external surface of a housing of said stimulator, wherein said housing houses electrical circuitry configured to produce an electrical stimulation pulse and a power source configured and arranged to supply the electrical circuitry with power, wherein the housing comprises the substantially flat first external surface, a substantially flat second external surface that is opposite the first external surface, a substantially rounded third external surface, and a substantially rounded fourth external surface, wherein the third and fourth external surfaces couple the first external surface to the second external surface, and wherein the substantially flat first external surface is a top surface and the substantially flat second external surface is a bottom surface;
providing at least one additional electrode contact disposed, at least in part, on the substantially flat second external surface of the housing, on the substantially rounded third external surface of the housing, or on both the second and third external surfaces;
implanting the stimulator within tissue of the patient near the stimulation site, wherein the stimulation site is a nerve, and
wherein said electrode contacts are configured to apply an electrical stimulation current to said stimulation site.

28. The method of claim 27, further comprising stimulating said stimulation site with one or more of a monopolar stimulation or a multipolar stimulation.

29. The method of claim 27, wherein said at least one electrode array is configured to have a first polarity that comprises a cathodic polarity and said at least one additional electrode is configured to have a second polarity that comprises an anodic polarity.

30. The method of claim 27, wherein said at least one electrode array is configured to have a first polarity that comprises an anodic polarity and said at least one additional electrode is configured to have a second polarity that comprises a cathodic polarity.

31. The method of claim 27, wherein said at least one additional electrode contact comprises a ring electrode contact that is disposed around a circumference of said housing of said stimulator on a portion of each of the first, second, third and fourth external surfaces.

32. The method of claim 27, wherein said at least one additional electrode contact comprises a stripe electrode that extends along a portion of a length of said housing of said stimulator.

33. The method of claim 27, wherein said at least one additional electrode contact comprises an array of individual electrode contacts.

34. The method of claim 33, wherein said individual electrode contacts are ganged.

35. The method of claim 27, wherein said electrode contacts are configured to deliver at least one or more of a bipolar stimulation or a tripolar stimulation.

36. The method of claim 27, wherein one or more of said multiple electrode contacts within said at least one electrode contact array are configured to have a polarity that is the same as the polarity of the at least one additional electrode contact.

37. The method of claim 27, wherein one or more of said multiple electrode contacts within said at least one electrode contact array and said at least one additional electrode contact are configured to deliver an electrical stimulation current to one or more stimulation sites.

38. The method of claim 27, further comprising adjusting a distance between said at least one electrode contact array and said at least one additional electrode contact to minimize a threshold current value.

* * * * *